(12) United States Patent
Marceglia et al.

(10) Patent No.: US 11,318,309 B2
(45) Date of Patent: May 3, 2022

(54) METHOD AND APPARATUS FOR TREATING TOURETTE SYNDROME BY BRAIN STIMULATION

(71) Applicant: NEWRONIKA S.P.A., Milan (IT)

(72) Inventors: Sara Renata Francesca Marceglia, La Spezia (IT); Alberto Priori, Virgilio (IT); Mattia Arlotti, Rimini (IT)

(73) Assignee: Newronika S.P.A., Milan (IT)

( * ) Notice: Subject to any disclaimer, the term of this patent is extended or adjusted under 35 U.S.C. 154(b) by 170 days.

(21) Appl. No.: 16/706,552

(22) Filed: Dec. 6, 2019

(65) Prior Publication Data

US 2020/0188675 A1    Jun. 18, 2020

Related U.S. Application Data

(60) Provisional application No. 62/779,216, filed on Dec. 13, 2018.

(51) Int. Cl.
*A61N 1/36* (2006.01)
*A61N 1/05* (2006.01)

(52) U.S. Cl.
CPC ....... *A61N 1/36082* (2013.01); *A61N 1/0534* (2013.01); *A61N 1/36135* (2013.01);
(Continued)

(58) Field of Classification Search
CPC .............. A61N 1/36082; A61N 1/0534; A61N 1/36175; A61N 1/36178; A61N 1/36171;
(Continued)

(56) References Cited

U.S. PATENT DOCUMENTS 5,683,422 A    11/1997   Rise
6,360,122 B1    3/2002   Fischell et al.
(Continued)

FOREIGN PATENT DOCUMENTS

EP    2 004 036 B1    7/2011
EP    1 940 508 B1   12/2011
(Continued)

OTHER PUBLICATIONS

BioWorld MedTech (2019). Cortera WAND Technology, Clarivate Analytics, 10 total pages.
(Continued)

*Primary Examiner* — Paula J Stice
(74) *Attorney, Agent, or Firm* — Cooley LLP

(57) ABSTRACT

Disclosed herein are deep-brain stimulation (DBS) systems and methods for the treatment of Tourette Syndrome (TS). The DBS methods described herein comprise a stimulation paradigm that may help to reduce the frequency and/or severity of motor and vocal tics, as well as rapid and involuntary muscle motions that are characteristic of TS. One variation of a method for the treatment of TS comprises adjusting electrical stimulation to a target brain region based on changes or variations in the neural activity signals in the target brain region. One example of a method described herein comprises monitoring the power values (e.g., spectral power values) of one or more frequency bands of the acquired neural activity signals and adjusting electrical stimulation parameters based on at least one variation or change of the monitored power values.

27 Claims, 7 Drawing Sheets

(52) U.S. Cl.
CPC ..... *A61N 1/36171* (2013.01); *A61N 1/36175* (2013.01); *A61N 1/36178* (2013.01)

(58) Field of Classification Search
CPC ............ A61N 1/36135; A61N 1/36139; A61N 1/36067; A61N 1/0529; A61N 1/0531; A61N 1/36025
See application file for complete search history.

(56) References Cited

U.S. PATENT DOCUMENTS

| | | |
|---|---|---|
| 6,366,813 B1 | 4/2002 | DiLorenzo |
| 6,473,639 B1 | 10/2002 | Fischell et al. |
| 6,480,743 B1 | 11/2002 | Kirkpatrick et al. |
| 6,820,019 B1 | 11/2004 | Kelly et al. |
| 6,873,872 B2 | 3/2005 | Gkuckman et al. |
| 6,993,384 B2 | 1/2006 | Bradley et al. |
| 7,024,247 B2 | 4/2006 | Gliner et al. |
| 7,089,059 B1 | 8/2006 | Pless |
| 7,127,296 B2 | 10/2006 | Bradley |
| 7,177,678 B1 | 2/2007 | Osorio et al. |
| 7,231,254 B2 | 6/2007 | DiLorenzo |
| 7,236,830 B2 | 6/2007 | Gliner |
| 7,277,758 B2 | 10/2007 | DiLorenzo |
| 7,385,443 B1 | 6/2008 | Denison |
| 7,620,456 B2 | 11/2009 | Gliner et al. |
| 7,787,958 B2 | 8/2010 | Stevenson |
| 7,847,628 B2 | 12/2010 | Denison |
| 8,019,419 B1 | 9/2011 | Panescu et al. |
| 8,078,281 B2 | 12/2011 | Priori et al. |
| 8,135,473 B2 | 3/2012 | Miesel et al. |
| 8,190,251 B2 | 5/2012 | Molnar et al. |
| 8,224,452 B2 | 7/2012 | Pless et al. |
| 8,280,514 B2 | 10/2012 | Lozano et al. |
| 8,396,565 B2 | 3/2013 | Singhal et al. |
| 8,423,145 B2 | 4/2013 | Pless et al. |
| 8,473,063 B2 | 6/2013 | Gupta et al. |
| 8,504,154 B2 | 8/2013 | Wanasek |
| 8,521,294 B2 | 8/2013 | Sarma et al. |
| 8,543,221 B2 | 9/2013 | Campbell et al. |
| 8,594,795 B2 | 11/2013 | Tcheng et al. |
| 8,644,930 B2 | 2/2014 | Kelly |
| 8,679,038 B1 | 3/2014 | Giuffrida |
| 8,718,757 B2 | 5/2014 | Bradley et al. |
| 8,744,587 B2 | 6/2014 | Miesel et al. |
| 8,825,175 B2 | 9/2014 | King |
| 8,892,208 B2 | 11/2014 | Flynn et al. |
| 8,942,809 B2 | 1/2015 | Assaf et al. |
| 8,954,152 B2 | 2/2015 | Gupta et al. |
| 8,983,617 B2 | 3/2015 | Chavan et al. |
| 9,002,449 B2 | 4/2015 | Kameli |
| 9,061,140 B2 | 6/2015 | Shi et al. |
| 9,089,704 B2 | 7/2015 | Kelly |
| 9,119,964 B2 | 9/2015 | Marnfeldt |
| 9,192,760 B2 | 11/2015 | Bradley et al. |
| 9,211,417 B2 | 12/2015 | Heldman et al. |
| 9,238,138 B2 | 1/2016 | Lee et al. |
| 9,248,280 B2 | 2/2016 | Moffitt et al. |
| 9,375,582 B2 | 6/2016 | Kaula et al. |
| 9,381,356 B2 | 7/2016 | Parker et al. |
| 9,399,132 B2 | 7/2016 | Parramon et al. |
| 9,421,379 B2 | 8/2016 | Zhu |
| 9,445,730 B2 | 9/2016 | Snyder et al. |
| 9,504,832 B2 | 11/2016 | Libbus et al. |
| 9,521,979 B2 | 12/2016 | Stanslaski et al. |
| 9,522,278 B1 | 12/2016 | Heldman et al. |
| 9,656,089 B2 | 5/2017 | Yip et al. |
| 9,750,938 B2 | 9/2017 | Ternes et al. |
| 9,844,676 B2 | 12/2017 | Zhang et al. |
| 9,888,861 B2 | 2/2018 | Carlson et al. |
| 10,219,697 B2 | 3/2019 | Muller |
| 10,596,379 B2 | 3/2020 | Arlotti et al. |
| 10,933,243 B2 | 3/2021 | Senderowicz et al. |
| 2001/0029391 A1 | 10/2001 | Gluckman et al. |
| 2002/0177882 A1 | 11/2002 | DiLorenzo |
| 2003/0114886 A1 | 6/2003 | Gluckman et al. |
| 2004/0073273 A1 | 4/2004 | Gluckman et al. |
| 2005/0065427 A1 | 3/2005 | Magill et al. |
| 2007/0162086 A1 | 7/2007 | DiLorenzo |
| 2007/0225674 A1 | 9/2007 | Molnar et al. |
| 2008/0269836 A1 | 10/2008 | Foffani et al. |
| 2009/0099627 A1 | 4/2009 | Molnar et al. |
| 2010/0114237 A1 | 5/2010 | Giftakis et al. |
| 2010/0327887 A1 | 12/2010 | Denison et al. |
| 2016/0242645 A1 | 8/2016 | Muller |
| 2018/0085572 A1 | 3/2018 | Stanslaski et al. |
| 2019/0269916 A1 | 9/2019 | Senderowicz et al. |
| 2020/0188675 A1 | 6/2020 | Marceglia et al. |
| 2020/0254261 A1 | 8/2020 | Arlotti et al. |
| 2021/0154476 A1 | 5/2021 | Senderowicz et al. |

FOREIGN PATENT DOCUMENTS

| | | |
|---|---|---|
| IT | MI-2015A000219 | 2/2016 |
| WO | WO-00/07494 A2 | 2/2000 |
| WO | WO-00/07494 A3 | 2/2000 |
| WO | WO-2007/049105 A1 | 5/2007 |
| WO | WO-2013/123112 A1 | 8/2013 |
| WO | WO-2015/069797 A1 | 5/2015 |
| WO | WO-2016/132258 A1 | 8/2016 |
| WO | WO-2018/064193 A1 | 4/2018 |

OTHER PUBLICATIONS

BioWorld MedTech (2018). UCSF Using Closed Loop Adaptive DBS, Clarivate Analytics, 24 total pages.

Bronstein, J.M. et al. (2011). "Deep Brain Stimulation for Parkinson Disease," Archives of Neurology 68:165-171.

Brown, P. et al. (2005). "Basal Ganglia Local Field Potential Activity: Character and Functional Significance in the Human," Clinical Neurophysiology 116:2510-2519.

Brown, P. et al. (2001). "Dopamine Dependency of Oscillations Between Subthalamic Nucleus and Palladium in Parkinson's Disease," J. Neurosci. 21:1033-1038.

Brown, P. (2003). "Oscillatory Nature of Human Basal Ganglia Activity; Relationship to the Pathophysiology of Parkinson's Disease," Mov. Disord. 18:357-363.

Burgess, J.G. et al. (2010). "Identifying Tremor-Related Characteristics of Basal Ganglia Nuclei During Movement in the Parkinsonian Patient," Parkinsonism & Related Disorders 16:671-675.

Cassidy, M. et al. (2002). "Movement-Related Changes in Synchronization in the Human Basal Ganglia," Brain 125:1235-1246.

Chang, S.Y. et al. (2013). "Development of the Mayo Investigational Neuromodulation Control System: Toward a Closed-Loop Electrochemical Feedback System for Deep Brain Stimulation," Journal of Neurosurgery 119:1556-1565.

Cogan, S.F. (2008). "Neural stimulation and recording electrodes," Annu Rev Biomed Eng. 10:275-309.

De Hemptinne, C. et al. (2015). "Therapeutic Deep Brain Stimulation Reduces Cortical Phase-Amplitude Coupling in Parkinson's Disease," Nature Neuroscience 18:779-786.

Denison, T. et al. (2007). "A 2 µW100 nV/rtHz chopper-stabilized instrumentation amplifier for chronic measurement of neural filed potentials," IEEE J. of Solid-State Circuits 42:2934-2945.

Doyle, L.M.F. et al. (2005). "Levodopa-Induced Modulation of Subthalamic Beta Oscillations During Self-Paced Movements in Patients With Parkinson's Disease," Eur. J. Neurosci. 21:1403-1412.

Eusebio, A et al. (2011). "Deep Brain Stimulation Can Suppress Pathological Synchronisation in Parkinsonian Patients," J. of Neurol. Neurosurgery & Psychiatry 82:569-573.

Foffani, G. et al. (2003). "300-HZ Subthalamic Oscillations in Parkinson's Disease," Brain 126:2153-2163.

Foffani, G. et al. (2004). "Adaptive Autoregressive Identification With Spectral Power Decomposition for Studying Movement-Related Activity in Scalp EEG Signals and Basal Ganglia Local Field Potentials," J. Neural Eng. 1:165-173.

Foffani, G. et al. (2005). "Physiological Recordings From Electrodes Implanted in the Basal Ganglia for Deep Brain Stimulation

(56) References Cited

OTHER PUBLICATIONS in Parkinson's Disease. The Relevance of Fast Subthalamic Rhythms," Acta Neurochir. Suppl. 93:97-99.

Foffani, G. et al. (2005). "Altered Subthalamo-Pallidal Synchronisation in Parkinsonian Dyskinesias," J. Neural Neurosurg. Psychiatry 76:426-428.

Foffani, G. et al. (2005). "Movement-Related Frequency Modulation of Beta Oscillatory Activity in the Human Subthalamic Nucleus," J. Physiol. 568:699-711.

Fogelson, N. et al. (2005). "Reciprocal Interactions Between Oscillatory Activi-ties of Different Frequencies in the Subthalamic Region of Patients With Parkinson's Disease," Eur. J. Neurosci. 22:257-266.

Hamani, C. et al. (2005). "Bilateral subthalamic nucleus stimulation for Parkinson's disease: A systematic review of the clinical literature," Neurosurgery 56:1313-1321.

International Search Report dated May 16, 2019, for PCT Application No. PCT/IB2019/051428, filed on Feb. 21, 2019, 3 pages.

International Search Report dated May 18, 2016, for PCT Application No. PCT/IB2016/050735, filed on Feb. 11, 2016, 7 pages.

Kühn, A.A. et al. (2009). "Pathological Synchronisation in the Subthalamic Nucleus of Patients With Parkinson's Disease Relates to Both Bradykinesia and Rigidity," Exp. Neurology 215:380-387.

Kühn, A.A. et al. (2005). "The Relationship Between Local Field Potential and Neuronal Discharge in the Subthalamic Nucleus of Patients With Parkinson's Disease," Experimental Neurology 194:212-220.

Kühn, A.A. et al. (2004). "Event-Related Beta Desynchronization in Human Subthalamic Nucleus Correlates With Motor Performance," Brain 127:735-746.

Levy, R. et al. (2002). "Dependence of Subthalamic Nucleus Oscillations on Movement and Dopamine in Parkinson's Disease," Brain 125:1196-1209.

Limousin, P. et al. (1996). "Abnormal Involuntary Movements Induced by Subthalamic Nucleus Stimulation in Parkinsonian Patients," Movement Disorders 11:231-235.

Modolo, J. et al. (2010). "Past, present and future of bran stimulation," Mathematical modelling of Natural Phenomena 5:185-207.

Modolo, J. et al. (2010). "Model-driven therapeutic treatment of neurological disorders: Reshaping brain rhythms with neuromodulation," Interface Focus 1:61-74.

Moro, E. et al. (2006). "Subthalamic Nucleus Stimulation: Improvements in Outcome With Reprogramming," Archives of Neurol. 63:1266-1272.

Notice of Allowance dated Nov. 14, 2019, for U.S. Appl. No. 15/550,284, filed Aug. 10, 2017, 7 pages.

Notice of Allowance dated Jun. 17, 2020, for U.S. Appl. No. 16/282,167, filed Feb. 21, 2019, 8 pages.

Pedram, A. et al. (2013). "A translational platform for prototyping closed-loop neuromodulation systems," Frontiers in Neural Circuits 6:117.

Priori, A et al. (2004). "Rhythm-Specific Pharmacological Modulation of Subthalamic Activity in Parkinson's Disease," Experimental Neurology 189:369-379.

Priori, A et al. (2013). "Adaptive Deep Brain Stimulation (aDBS) Controlled by Local Field Potential Oscillations," Experimental Neurology 245:77-86.

Priori, et al, "Movement-Related Modulation of Neural Activity in Human Basal Ganglia and its L-Dopa Dependency: Recordings From Deep Brain Stimulation Electrodes in Patients With Parkinson's Disease", Neurol. Sci., Sep. 2002, pp. S101-S102.

Qian, X. et al. (2017). "A Method for Removal of Deep Brain Stimulation Artifact from Local Field Potentials," IEEE Trans. on Neural Systems and Rehabilitation Engineering, 25(12), 2217-2226.

Rosin, B. et al. (2011). "Closed-Loop Deep Brain Stimulation Is Superior in Ameliorating Parkinsonism," Neuron 72:370-384.

Santaniello, S. et al. (2011). "Closed-Loop Control of Deep Brain Stimulation: A Simulation Study," IEEE Transactions on Neural Systems and Rehabilitation Engineering 19:15-24.

Silberstein, P. et al. (2003). "Patterning of Globus Pallidus Local Field Poten-tials Differs Between Parkinson's Disease and Dystonia," Brain 126:2597-2608.

Stanslaski, S. et al. (2011). "Design and validation of a fully implantable, chronic, closed-loop neuromodulation device with concurrent sensing and stimulation," IEEE Trans Neural Syst Rehabil Eng. 20:410-421.

Williams, D. et al. (2002). "Dopamine-Dependent Changes in the Functional Connectivity Between Basal Ganglia and Cerebral Cortex in Humans," Brain 125:1558-1569.

Written Opinion of the International Searching Authority dated May 16, 2019, for PCT Application No. PCT/IB2019/051428, filed on Feb. 21, 2019, 5 pages.

Written Opinion of the International Searching Authority dated May 18, 2016, for PCT Application No. PCT/IB2016/050735, filed on Feb. 11, 2016, 8 pages.

Yoshida, F. et al. (2010). "Value of Subthalamic Nucleus Local Field Potentials Recordings in Predicting Stimulation Parameters for Deep Brain Stimulation in Parkinson's Disease," Journal of Neurology, Neurosurgery & Psychiatry 81:885-889.

Zhou, A. et al. (2019). "A wireless and artefact-free 128-channel neuromodulation device for closed-loop stimulation and recording in non-human primates," Nature Biomedical Engin. 3:15-26.

Zhou, A. et al. (2017). WAND: A 128-channel, closed-loop, wireless artifact-free neuromodulation device, 30 total pages.

Zhao-Hui, W. et al. (2015). "Implantable analog front-end with high PSRR and CMRR for neural signal acquisition," Journal of South China University of Technology (Natural Science Edition) 43:15-20 (English Abstract Provided).

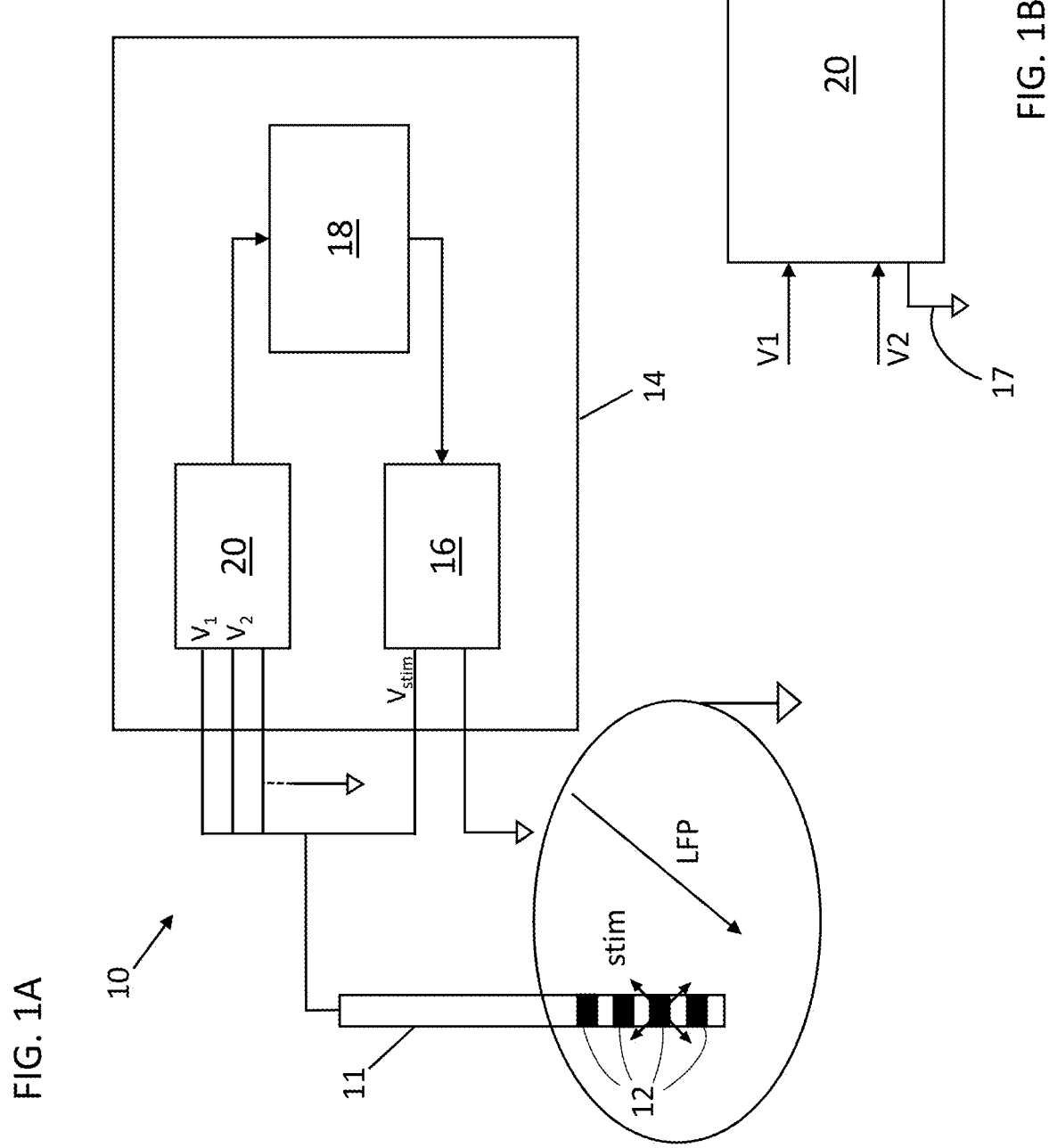

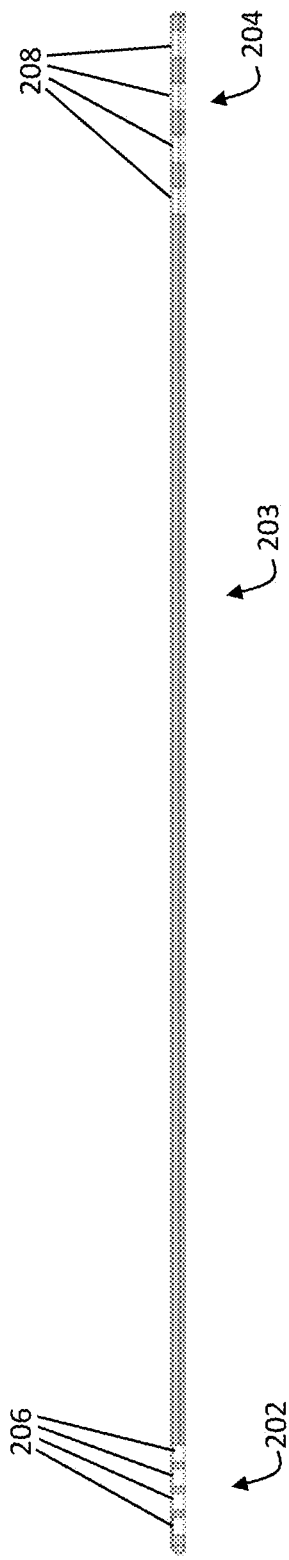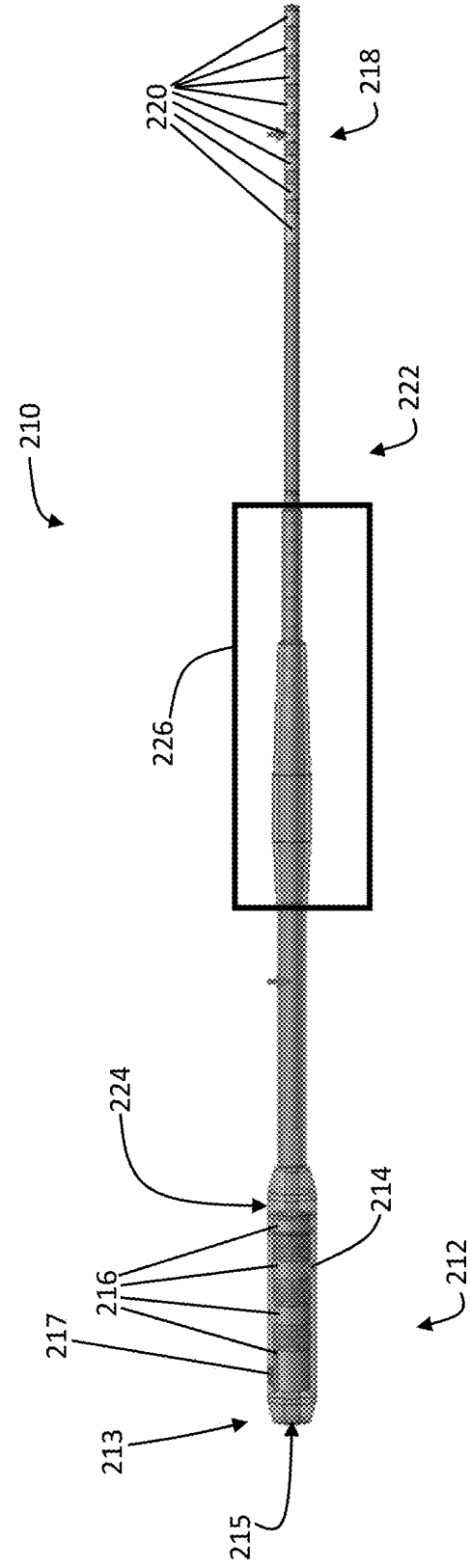

METHOD AND APPARATUS FOR TREATING TOURETTE SYNDROME BY BRAIN STIMULATION

CROSS-REFERENCE TO RELATED APPLICATIONS

This application claims priority to U.S. Provisional Patent Application No. 62/779,216, filed Dec. 13, 2018, which is hereby incorporated by reference in its entirety.

BACKGROUND

Tourette Syndrome (TS) is a common neuropsychiatric disorder that often presents in childhood and is characterized by multiple motor tics and/or vocal (phonic) tics. Tics are sudden, repetitive, non-rhythmic movements (motor tics) or utterances (phonic tics), each affecting a sub-set of muscles. Motor tics are movement-based tics, while phonic tics are involuntary sounds produced by moving air through the nose, mouth, or throat. Co-occurring disorders of attention and impulse control are also common, including attention deficit hyperactivity disorder and obsessive-compulsive disorder.

In some individuals, TS symptoms improve in adolescence and the number and/or severity of tics decline (or even cease entirely) in adulthood. However, in some individuals, the tics persist even in adulthood, and may even increase in number and severity, thus requiring long-term treatment. In recent years, deep brain stimulation (DBS) has emerged as a promising therapeutic approach for treating TS.

DBS delivers electrical stimulation to neural structures of the central nervous system to modulate neural activity. Probes comprising one or more electrodes are implanted into a target region within the brain of the patient. The target region selected for DBS is usually directly or indirectly responsible for the disease symptoms, and the aim of DBS is to reduce the frequency and/or severity of the symptoms by electrically modulating the neural circuits in or around the target region.

DBS consists of generating a train of electric pulses using a pulse or function generator that is connected to the implanted probe. The probe delivers the electric pulses to the brain target region via one or more electrodes on the probe. In many applications, the pulse frequency is greater than about 100 Hz, and has a biphasic waveform with a cathodic phase followed by an anodic phase, which are charge-balanced to avoid tissue damage. Typically, the pulse train is continuously applied to the target region, but in some applications, the pulse train is applied intermittently and/or applied on a schedule. In a scheduled stimulation time paradigm, DBS is delivered following an a-priori determined schedule that has a reduced stimulation time as compared to the continuous DBS paradigm.

It has been found that scheduled or intermittent DBS has had some positive effect on addressing the tics arising from TS. One study found that the Yale Global Tic Severity Scale (YGTSS) can be significantly improved with an average of 2.3 h/day of DBS stimulation over two years. While intermittent or scheduled DBS may provide some therapeutic effect and may prolong battery life (as compared to continuous DBS), further improvements to methods for treating TS are desirable.

SUMMARY

Disclosed herein are DBS systems and methods for the treatment of Tourette Syndrome (TS). The DBS methods described herein comprise a stimulation paradigm that may help to reduce the frequency and/or severity of motor and vocal tics, as well as rapid and involuntary muscle motions that are characteristic of TS. One variation of a DBS system may comprise a probe having one or more electrodes and a pulse or function generator in electrical communication with the probe. The probe may be configured to be implanted in a brain region having neural circuits or structures that underlie the various symptoms linked to TS. The pulse generator may comprise a voltage source and circuitry configured to produce electrical pulses with certain parameter values determined by a user and/or control module, and may also comprise wires that transmit the electrical pulses to the probe, which are configured to deliver the electrical pulses to the brain region. Alternatively or additionally, a DBS system may comprise a data acquisition module that is in electrical communication with a probe which may be, in some variations, the same probe used to electrically stimulate the brain region. The acquisition module and/or the probe may be configured to acquire neural activity signals, such as local-field potentials (LFPs), resulting from the activity of the brain region in proximity to the probes. The acquisition module may comprise a controller having a processor and memory that stores and analyzes the acquired neural activity signals and may be configured to adjust electrical stimulation parameters according to the recorded LFPs.

Also disclosed herein are methods for adjusting electrical stimulation to the brain region based on changes or variations in the neural activity signals to address symptoms associated with TS. Methods may comprise monitoring the power values (e.g., spectral power values) of one or more frequency bands of the acquired neural activity signals, and adjusting electrical stimulation parameters based on at least one variation or change of the monitored power values. Power variations in certain frequency bands may correlate with one or more symptoms of TS, and may, for example, provide an indication of an upcoming tic (and/or a tic that is currently in-progress). One variation of a method for treating TS may comprise acquiring neural activity signals from the implanted probe, determining a power value of the acquired signal in a first frequency band, determining whether a decrease of the power value in the first frequency band with respect to a first baseline value is followed by an increase of the power value of the first frequency band, and if a decrease of the power value is followed by an increase of the power value in the first frequency band, modifying the electrical stimulation signal parameters according to the acquired neural activity signal. In some variations, the method may comprise modifying initial or baseline stimulation parameters (i.e., stimulation parameter values for stimulation in the absence of a TS symptom).

One variation of a method for treating Tourette Syndrome may comprise acquiring an electrical neural activity signal using at least one electrode implanted in a brain of a patient and monitoring a first power of the acquired neural activity signal in a first frequency band, identifying the occurrence of a tic by determining whether a decrease of the first power with respect to a first baseline value for a first predetermined duration is followed by an increase in the first power with respect to the first baseline value for a second predetermined duration, and if the occurrence of a tic is identified, modifying a parameter of electrical stimulation to the brain according to acquired neural activity signal. Optionally, the method may comprise determining a second power of the acquired neural activity signal in a second frequency band, determining whether an increase of the second power for a third predetermined duration with respect to a second baseline value occurs simultaneously with the decrease of the first power, and if an increase of the second power with respect to the second baseline value occurs simultaneously with the decrease of the first power, modifying the electrical stimulation parameter according to acquired neural activity signal. The first predetermined duration may be at least about 250 ms, and the second predetermined duration may be at least about 250 ms. The increase in the first power may be at least about 2.5 times greater than the first baseline value. In some variations, the decrease of the first power may be at least about 20% below the first baseline value and the following increase of the first power may be at least about 150% above the first baseline value. The first frequency band may comprise frequencies in the alpha band (about 8 Hz to about 12 Hz) and/or the second frequency band may comprise frequencies in the low-frequency band (about 2 Hz to about 7 Hz). The electrical stimulation parameter may be an electrical pulse frequency, and modifying the parameter value may comprise assigning the electrical pulse frequency to a frequency value from about 30 Hz to about 40 Hz. Alternatively or additionally, the electrical stimulation parameter may be an electrical pulse frequency, and modifying the parameter value may comprise assigning the electrical pulse frequency to a frequency value that is at least about 50% less than an initial electrical pulse frequency value. In some variations, the electrical stimulation parameter may be an electrical pulse width value, and modifying the parameter value may comprise assigning the electrical pulse width to a width value from about 10 μs to about 30 μs. In some variations, the first power of the acquired neural activity signal in the first frequency band is determined by applying a band pass filter, followed by a rectifier, followed by applying an average filter to the acquired neural activity signal.

The electrical neural activity signal may be acquired during the delivery of electrical stimulation to the brain having the electrical stimulation parameter assigned to an initial electrical stimulation parameter value, and in some variations, the method may further comprise delivering electrical stimulation to the brain having the modified electrical stimulation parameter. For example, the method may comprise acquiring an updated electrical neural activity signal during delivery of electrical stimulation signal having the modified electrical stimulation parameter and monitoring the first power of the updated electrical neural activity signal in the first frequency band, determining whether the first power has returned to approximately the first baseline value, and if the first power has returned to approximately the first baseline value, delivering electrical stimulation to the brain having the initial electrical stimulation parameter value. In some variations, if the first power has returned to within about 50% of the first baseline value, the method may comprise delivering electrical stimulation to the brain having the initial electrical stimulation parameter value.

Also described herein are systems for the treatment of Tourette Syndrome. One variation of an apparatus for the treatment of Tourette Syndrome may comprise an implantable probe comprising an electrode, and a stimulation device in communication with the implantable probe. The stimulation device may comprise a stimulation module having circuitry configured to generate a stimulation signal to be transmitted to the electrode, the stimulation signal having an electrical stimulation parameter, an acquisition module having circuitry configured to acquire a neural activity signal from the electrode and to identify a tic occurrence and to modify the electrical stimulation parameter if the occurrence of a tic is identified, and a control module having circuitry configured to communicate the modified electrical stimulation parameter to the stimulation module to modify the stimulation signal generated by the stimulation module to have the modified electrical stimulation parameter. The acquisition module may be configured to identify the occurrence of a tic by determining whether a decrease of a first power of the acquired neural activity signal with respect to a first baseline value for a first predetermined duration is followed by an increase in the first power with respect to the first baseline value for a second predetermined duration. The control module may further comprise a memory element configured to store the modified electrical stimulation parameter and an initial electrical stimulation parameter. Optionally, identifying the occurrence of a tic may further comprise determining whether a second power of the acquired neural activity signal in a second frequency band increases for a third predetermined duration with respect to a second baseline value simultaneously with the decrease of the first power. In some variations, the first predetermined duration may be at least about 250 ms, and the second predetermined duration may be at least about 250 ms. The increase in the first power may be at least about 2.5 times greater than the first baseline value. Alternatively or additionally, the decrease of the first power may be at least about 20% below the first baseline value and the following increase of the first power may be at least about 150% above the first baseline value. The first frequency band may comprise frequencies in the alpha band (about 8 Hz to about 12 Hz) and/or the second frequency band may comprise frequencies in the low-frequency band (about 2 Hz to about 7 Hz). The electrical stimulation parameter may be an electrical pulse frequency, and modifying the parameter value may comprise assigning the electrical pulse frequency to a frequency value from about 30 Hz to about 40 Hz. In some variations, the acquisition module circuitry may comprise a band pass filter, a rectifier, and an average filter for determining the first power of the acquired neural activity signal in the first frequency band.

In some variations, the electrical stimulation parameter may be an electrical pulse frequency and the initial electrical stimulation parameter may be an initial electrical pulse frequency value, and modifying the parameter value may comprise assigning the electrical pulse frequency to a frequency value that is about 50% less than the initial electrical pulse frequency value. The electrical stimulation parameter may be an electrical pulse width value, and modifying the parameter value may comprise assigning the electrical pulse width to a width value from about 10 μs to about 30 μs. The acquisition module circuitry may be further configured to identify a tic conclusion by determining whether the first power has returned to approximately the first baseline value. The acquisition module circuitry may optionally be configured to modify the stimulation signal generated by the stimulation module to have the initial electrical stimulation parameter if a tic conclusion is identified. For example, a tic conclusion may be identified if the first power has returned to within about 50% of the first baseline value.

BRIEF DESCRIPTION OF THE DRAWINGS

One or more features of each embodiment or variation described herein may be unrestrictedly and independently combined with each other in order to achieve the advantages derived by such combination.

FIG. 1A depicts a schematic view of one variation of a system for treating Tourette Syndrome;

FIG. 1B depicts a block diagram of an acquisition module adopted by the system of FIG. 1A;

FIG. 2A depicts one variation of a probe comprising electrodes for acquiring neural activity data and/or delivering electrical stimulation;

FIG. 2B depicts one variation of a connector or probe extension for use with a probe;

FIG. 3A depicts the power spectrum of LFPs measured from the Vo/CM-Pf nucleus acquired by electrode contacts 0 and 1 (solid line), 1 and 2 (dashed line), and 2 and 3 (dotted line);

FIG. 3B depicts plots of LFP power modulations for the low-frequency band (left), alpha band (center), and high beta band (right) recorded during upper limb tics from the electrode contact pairs 0 and 1 (solid line) and 1 and (dashed line), averaged across all observed tics, where the power modulations are expressed as percentage changes (e.g., Hilbert-power modulations) from the baseline phase and estimated starting 1.5 s before the movement onset until 2 s after the movement onset; movement-related phases are indicated as baseline (b), pre-movement (p), movement (m), and recovery (r);

FIG. 3C depicts plots of LFP power modulations for the low-frequency band (left), alpha band (center), and high beta band (right) recorded during lower limb tics from the electrode contact pairs 0 and 1 (solid line) and 1 and (dashed line), averaged across all observed tics, where the power modulations are expressed as percentage changes (e.g., Hilbert-power modulations) from the baseline phase and estimated starting 1.5 s before the movement onset until 2 s after the movement onset;

DETAILED DESCRIPTION

Figure 1C:
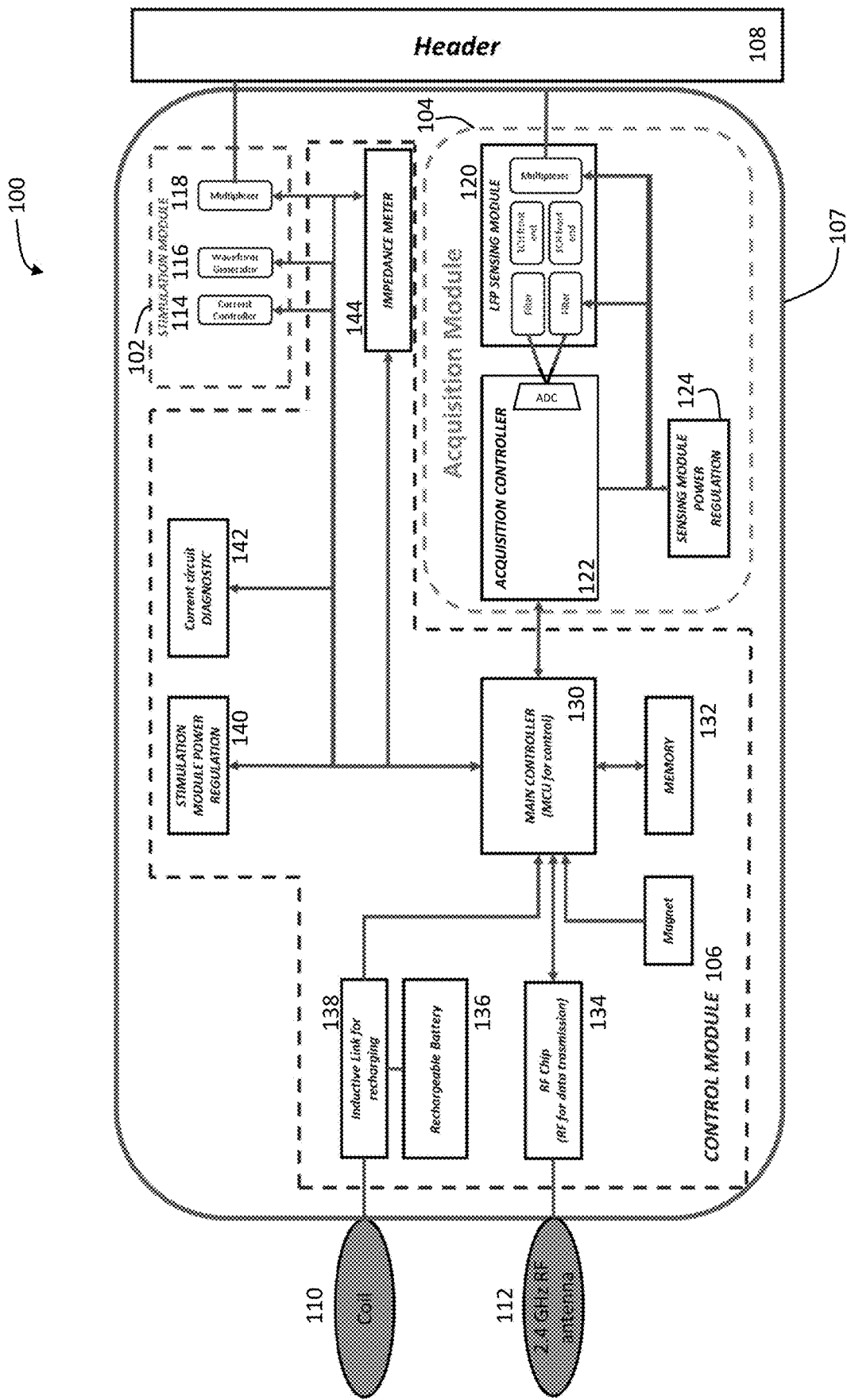
FIG. 1C depicts a block diagram of one variation of a system for treating Tourette Syndrome.

Disclosed herein are systems and methods for the treatment of Tourette Syndrome (TS). The DBS methods described herein comprise a stimulation paradigm that may help to reduce the frequency and/or severity of motor and vocal tics, rapid and involuntary muscle motions that are characteristic of TS, along with neuropsychiatric and/or physical comorbidities that may be associated with TS. One variation of a system may comprise a probe having one or more electrodes and a stimulation module in electrical communication with the probe. The probe may be configured to be implanted in a brain region having neural circuits or structures that underlie the various symptoms linked to TS. The stimulation module may comprise pulse or function generator comprising a voltage source and/or current source and circuitry configured to produce electrical pulses with certain parameter values determined by a user and/or controller, and may also comprise wires that transmit the electrical pulses to the probe, which deliver the electrical pulses to the brain region. Alternatively or additionally, a DBS system may comprise a data acquisition module that is in electrical communication with a probe which may be, in some variations, the same probe used to electrically stimulate the brain region. The acquisition module and/or the probe may be configured to acquire neural activity signals, such as local-field potentials (LFPs), resulting from the activity of the brain region in proximity to the probes. The acquisition module may comprise an acquisition processor and memory that stores and analyzes the acquired neural activity signals. The DBS system may also comprise a control module having circuitry configured to facilitate communication between the acquisition module and the stimulation module, coordinate signalling between the acquisition module and the stimulation module, and/or to perform additional computations on the acquired neural activity signals.

Also disclosed herein are methods for closed-loop, adaptive DBS (aDBS) to address symptoms associated with TS. Closed-loop aDBS may comprise adapting stimulation parameters (e.g., pulse amplitude, frequency, duty cycle, polarity, and/or any waveform characteristics and so on) according to changes in the pattern of neural activity signals. In other words, closed-loop aDBS may comprise measuring and analyzing a control variable that may represent a patient's clinical condition, and adjusting stimulation settings. In some variations, the adjustment of stimulation settings may take place concurrently with measuring the control variable. Adapting stimulation parameters according to a patient's clinical condition as indicated by the measured neural activity signals may help to improve the treatment efficacy. In some variations, aDBS may comprise detecting patterns of neural activity linked to the onset of a tic and applying electrical stimulation to prevent, or otherwise mitigate, the tic. Neural activity signals (i.e., local field potentials) may be recorded using one or more implanted probes (each having one or more electrodes). Local field potentials (LFPs) are electrical signals that represent a sum of pre- and post-synaptic activities which arise from a neuronal population. In some variations, the electrodes of a stimulation probe may also be configured to acquire neural activity signal data while also applying electrical stimulation at the same time.

One variation of a method for alleviating symptoms associated with TS may comprise adjusting electrical stimulation to the brain region based on changes or variations in the neural activity signals. For example, methods may comprise monitoring the power values of one or more frequency bands of the acquired neural activity signals, and adjusting electrical stimulation parameters based on at least one variation of the monitored power values. Power variations in certain frequency bands may correlate with one or more symptoms of TS, and may, for example, provide an indication of an upcoming tic (and/or a tic that is currently in-progress). One variation of a method for treating TS may comprise acquiring neural activity signals from the implanted probe, determining a power of the acquired signal in a first frequency band, determining whether a decrease of the power in the first frequency band with respect to a first baseline value is followed by an increase of the power of the first frequency band, and if a decrease of the power is followed by an increase of the power in the first frequency band, modifying the plurality of initial stimulation signal parameters according to the acquired neural activity signal.

While the variations of the DBS systems described and depicted herein are shown as having a single probe, it should be understood that a DBS system may comprise additional probes that are connected to a common and/or separate pulse or function generators. For example, a DBS system may comprise a first probe having one or more electrodes, a second probe having one or more electrodes, and a pulse generator that is in electrical communication with the first and second probes. Alternatively or additionally, a second pulse generator may be included such that the first probe is connected to the first pulse generator and the second probe is connected to the second pulse generator. The probes may be configured to acquire neural activity signals while applying electrical stimulation to the same brain region, and/or the first probe may be configured to acquire neural activity signals while the second probe may be configured to deliver electrical stimulation to the brain region.

In the figures and in the following description, identical reference numerals or symbols are used to indicate constructive elements with the same function. Moreover, for the sake of clarity of illustration, it is possible that some references are not repeated in all of the figures.

While the one or more inventions described herein may be subject to modifications, or be implemented in alternative ways, in the drawings some preferred embodiments are shown which will be discussed in detail in the following. However, it should be understood that there is no intention to limit the one or more inventions to the specific embodiments/variations described, but on the contrary, the one or more inventions may include all the modifications or alternative and equivalent implementations which fall within the scope of protection as defined in the claims.

Expressions like "example given", "etc.", "or" indicate non-exclusive alternatives without limitation, unless expressly differently indicated. Expressions like "comprising" and "including" have the meaning of "comprising or including, but not limited to" unless expressly differently indicated.

Systems

A system for deep-brain stimulation (DBS), which may be used for adaptive deep-brain stimulation, may comprise one or more electro-catheters or probes and a stimulation device in electrical communication with the one or more probes. Each probe may comprise one or more electrodes or electrical contacts/pads which are made of an electrically-conductive material configured to deliver electrical pulses and/or detect electrical activity of surrounding brain tissue. The stimulation device may comprise a control module and a stimulation module in electrical communication with the one or more probes. Optionally, the stimulation device may comprise an acquisition module that is also in electrical communication with the one or more probes. The stimulation module may comprise circuitry configured to produce electrical pulses with certain parameter values determined by a user and/or a controller (e.g., the control module and/or acquisition module). The control module may comprise a control module (main) processor and a memory, and may optionally comprise circuitry configured to regulate/coordinate the operation of the stimulation module based on signals from the acquisition module. The control module processor may comprise circuitry configured to determine electrical stimulation parameters and to generate command signals to the stimulation module to generate electrical stimulation having the determined stimulation parameters. The DBS system may also comprise wires that transmit the electrical pulses to the electrodes of the one or more probes. Optionally, one or more of the probes may be used for both neural activity signal acquisition and electrical stimulation. Any of the controller modules and/or processors described herein may include a microcontroller device or computing processor unit.

The stimulation module may comprise, for example, a pulse generator with a voltage source and/or current source that may produce electrical pulses having the parameter value(s) as determined by the control module. In some variations, a stimulation module may comprise a waveform generator (e.g., a pulse or function generator), a current controller, and a multiplexer, one or more of which may be configured to receive command signals from the control module or main processor. The command signals may comprise electrical stimulation parameter data, including, but not limited to, stimulation amplitude, pulse width, pulse frequency, duty cycle, and/or the specific probe(s) and/or electrode(s) from which electrical stimulation with the specified parameters is to be delivered. The current controller may be configured to set an electrical stimulation amplitude specified by the command signals, and/or the waveform generator may be configured to generate current or voltage pulses having the pulse width and/or pulse frequency specified by the command signals. The multiplexer may be configured to electrically connect the probes and/or electrodes specified by the command signals with the current controller and/or waveform generator. In some variations, the multiplexer may comprise a multiplexer array that may be configured according to command signals from the main processor so that the electrical pulses from the waveform generator may be channelled to the selected probes and/or electrodes. The connectivity between the waveform generator and the electrodes may be arranged by the multiplexer in a monopolar stimulation configuration and/or a bipolar stimulation configuration. In a monopolar configuration, one or more electrodes may be connected to one or more active (e.g., positive) terminals of the waveform generator (with a return pad placed elsewhere on a patient). In a bipolar configuration, a first set of one or more electrodes may be connected to one or more active (e.g., positive) terminals of the waveform generator while a second set of one or more electrodes (e.g. distinct from the first set of electrodes) may be connected to one or more return (e.g., negative) terminals of the waveform generator.

In some variations, a DBS system may comprise a stimulation device that may also comprise a data acquisition module that is in electrical communication with one or more of the probes. The data acquisition module may comprise sensing module comprising circuitry to multiplex between probes and/or electrodes, and an acquisition processor in communication with the sensing module comprising circuitry configured to analyze the LFPs (which represent neural activity from surrounding brain tissue) to identify patterns of neural activity that may be associate with a tic. The acquisition processor may also comprise circuitry configured to control a multiplexer array in the sensing module to select the one or more electrodes (e.g., electrode pair(s)) for LFP data acquisition. In some variations, the sensing module may comprise one or more filters that remove unwanted signal artifacts and/or noise from the raw LFPs and the acquisition processor may comprise an analog-to-digital converter to convert the filtered LFPs to digital signals for computational analysis. In some variations, the acquisition processor may be configured to calculate or otherwise determine electrical stimulation parameters based on the acquired neural activity signals. For example, an acquisition processor may be configured to extract the spectral power of each LFP signal for one or more frequency bands, and to calculate a set of electrical stimulation parameters based on the spectral power values of the one or more frequency bands. In some variations, the calculated stimulation parameters and/or the spectral power values and/or the acquired LFP signals may be transmitted to the controller module (main) processor. A data acquisition module may optionally comprise one or more memories to store the raw electrical signals and/or processed or transformed electrical signals. A data acquisition module may optionally comprise circuitry for regulating the power supply to the acquisition processor and the sensing module. In some variations, a DBS system may comprise a probe that is electrically connected to both the stimulation module (e.g., pulse generator) and the acquisition module. For example, a probe may be connected to the input ports of the acquisition module for gathering neural activity signals and connected to the output ports of the pulse generator to deliver electrical stimulation to the brain region from which the neural activity signals were gathered.

Some variations of a DBS system may comprise a control module (which may be part of either the acquisition module or the stimulation module, or may be a separate module) comprising circuitry configured to regulate/coordinate the operation of the stimulation module based on signals from the acquisition module (e.g., based on LFP signals indicative of neural activity). The control module may have a control module (main) processor and memory that analyzes and stores the acquired neural activity signals and/or signals from the acquisition module. In some variations, the control module may comprise circuitry that regulates the power supplied to the stimulation module, for example, in coordination with the electrical stimulation parameters determined by the acquisition module and/or the acquired neural activity signals. The properties or parameters of the electrical stimulation may be determined by the acquisition module and/or the control module. For example, the processors of the acquisition module and/or the control module may analyze the acquired and/or stored neural activity signals to identify variations or changes in the patterns or characteristics of neural activity signals. The control module may provide command signals to the pulse generator of the stimulation module to change the parameters of the electrical stimulation according to the changes in the neural activity signals detected or extracted by the acquisition module. The control module may also comprise a battery (e.g., a rechargeable battery), and circuitry configured to charge and/or measure the charge remaining on the battery. For example, the control module may comprise a rechargeable battery, an inductive link for charging the battery and an inductive coil for facilitating the energy transfer between an external charging device and the stimulation device (which may be implanted in the patient). Optionally, the control module may comprise wireless transmission interface (e.g., a transceiver) including an RF chip and an RF antenna for signal transmission between the implantable stimulation device and an external device. In some variations, the acquisition module may comprise a processor that is configured to calculate the spectral power values of acquired neural activity signals, and the calculated power values may be transmitted to the control module, and the control module processor may be configured to derive stimulation parameters according to the power values and general command signals to the pulse generator to adapt or adjust the parameters of the electrical stimulation. Optionally, the control module may comprise additional sub-modules with circuitry configured for power supply management, electrode impedance checking, and/or calibration and/or diagnostic analyses (e.g., troubleshooting) of the stimulation module.

A DBS system may comprise one or more implantable probes where each probe may comprise one or more electrodes. The system may also comprise a connector or probe extension for each of the implantable probes. A probe may have a distal portion and a proximal portion, where the one or more electrodes (for delivering electrical stimulation and/or neural activity data acquisition) are located on the distal portion and one or more connector contacts are located on the proximal portion and one or more wires within the probe electrically connect the electrodes with the connector contacts. A probe may comprise any number of electrodes, for example, 1, 2, 3, 4, 5, 6, 8, 10, 12, 16, 24, 36, 48, 64, 96, etc. and a corresponding number of connector contacts. A probe extension may have a distal portion having a connector block with a receptacle housing enclosing one or more conductive contacts, a proximal portion having stimulation device connector contacts, where each of the stimulation device connector contacts corresponds with a conductive contact in the receptacle housing via one or more wires, and an elongated body between the proximal portion and the distal portion. A probe extension may comprise any number of conductive contacts, for example, 1, 2, 3, 4, 5, 6, 8, 10, 12, 16, 24, 36, 48, 64, 96, etc. and a corresponding number of stimulation device connector contacts. The number of conductive contacts of the probe extension may be the same as, or greater than, the number of electrodes on the probe to which the probe extension is connected. The distal portion of the probe may be implantable into the target brain region, while the proximal portion of the probe may extend outside of the brain tissue and connect with a distal portion of a probe extension. The receptacle housing of the probe extension may be configured to retain the proximal portion of the probe such that the connector contacts of the probe electrically connect with the conductive contacts of the probe extension such that the electrodes at the distal portion of the probe are electrically coupled to the stimulation device connector contacts a the proximal portion of the probe extension. The stimulation device connector contacts may be configured to be coupled to a port or connector of the stimulation device (e.g., a header interface). In some variations, the receptacle housing may comprise an attachment mechanism to engage or retain the proximal portion of the probe within the receptacle housing. Optionally, the probe extension may comprise a connector sleeve or boot comprising an electrically insulating material that is disposed over at least a portion of the receptacle housing to help electrically isolate the connector contacts of the probe and the conductive contacts of the probe extension from surrounding tissue. The elongated body of the probe extension may have a constant diameter between the distal portion and the proximal portion, or may have a varying diameter along its length. For example, the diameter of a segment of the elongated body may be larger (e.g., thicker) where that segment is intended to be located at the interface between brain tissue and the skull or skin. This may help reduce excessive twisting, torqueing, and/or bending of the wires within the elongated body of the probe extension, thereby reducing the mechanical wear on the wires and/or helping to prolong the usable life of the probe extension.

FIG. 1A depicts one variation of a DBS system (10) for treating neurological disorders (e.g., TS). The DBS system (10) may comprise at least one electro-catheter or probe (11) configured to be implanted in the brain of a patient to administer electric stimulation. An electrode (12) may comprise a metallic contact or lead. While the system (10) comprises a probe (11) having four metallic contacts or electrodes (12), other variations of probes may comprise any number of electrodes (e.g., 1, 2, 3, 4, 5, 6, 7, 8, 9, 10, 12, 16, 18, 20, 25, 30, 36, 48, or more). As described previously, a DBS system may comprise any number of probes (e.g., two or more), where each probe may have any number of electrodes. For example, a DBS system may comprise a first probe with a first electrode and a second probe with a second electrode. In use, the first probe may be implanted in a first brain region and the second probe may be implanted in a second brain region (e.g., for bilateral stimulation). In another variation, a DBS system may comprise two probes, where each probe may have 4 electrodes (for a total of 8 channels) or may have 8 electrodes (for a total of 16 channels).

The system (10) may be configured for adaptive deep brain stimulation by detecting neural activity signals (e.g., LPFs, biopotentials) using one or more electrodes and delivering electrical stimulation using one or more electrodes. In one variation, a probe may comprise multiple electrodes where a first electrode is a stimulating electrode that delivers electrical stimulation and a second electrode is a measurement electrode that acquires neural activity signals. For example, a first plurality of electrodes (which may or may not be adjacent to each other) may be used for stimulating and a second plurality of electrodes (which may or may not be adjacent to each other, or may be arranged in alternating fashion with the first plurality of electrodes) may be used for acquiring neural activity signals. Alternatively or additionally, the same electrode(s) may be used for both neural activity signal acquisition and electrical stimulation simultaneously or sequentially. DBS probes may comprise one or more cylindrical or disc-shaped electrodes having a height from about 0.5 mm to about 3 mm, e.g., about 1.5 mm, and a diameter from about 0.5 mm to about 2 mm, e.g., about 1.27 mm. In some variations, DBS probes may comprise two or more cylindrical electrodes, for example, 2, 4, 6, 10, 12, 15, 16, 20, etc. or more electrodes. Alternatively or additionally, DBS probes may comprise planar electrodes and/or sharp electrodes having a geometry selected at least in part based on the target neural structure or brain region. The spacing between two electrodes may be from about 0.25 mm to about 2 mm, e.g., about 0.5 mm, and optionally, an insulator may be disposed between two electrodes and/or around an electrode to reduce electrical coupling or cross-talk between electrodes. An insulator may comprise, for example, polyurethane and/or polyimide and/or the like. The electrodes may be made of any metal or any metallic alloy, for example, a platinum-iridium alloy.

The DBS system (10) may comprise a stimulation device (14) and the electrodes (12) may be electrically connected to the stimulation device (14) via one or more wires. In one variation, a stimulation device (14) may comprise 16 channels, which may be connected to 2 probes each having 8 electrodes, or 4 probes each having 4 electrodes, or 8 probes each having 2 electrodes, etc. There may be fewer electrodes than channels, for example, although the a stimulation device may be configured to accommodate 16 channels (e.g., for 16 stimulation and/or LFP acquisition electrodes), a particular instance of a DBS system may comprise 8 electrodes (e.g., 2 probes each having 4 electrodes) or 4 electrodes (e.g., a single probe having 4 electrodes). In some variations, a stimulation device comprises three sub-systems, components, or modules that are in communication with each other (e.g., connected together in feedback and interoperating). The stimulation device (14) of FIG. 1 may comprise a stimulation sub-system or module (16), an acquisition sub-system or module (20) and a control sub-system or module (18). The stimulation module (16) may comprise a pulse (or function) generator. For example, the stimulation module (16) may comprise a current source (and/or voltage source) and circuitry configured to generate a stimulation signal that is transmitted to the electrodes (12). The acquisition module (20) may comprise circuitry configured for the acquisition of LFP signals that may represent the cerebral activity in the brain region where the probe (11) is implanted. The control module (18) implements an adaptive control of the stimulation module (16) based on the neural activity signals acquired by the acquisition module (20). The control module (18) may comprise a processor and a memory that stores the acquired neural activity signal data from the electrodes (12) and the processor may be configured to analyze the acquired data to identify correlations between neural activity signals with the delivered electrical stimulation and to adapt the electrical stimulus parameters to facilitate mitigation of the symptoms and/or comorbidities of TS.

In some variations, the stimulation module (16) may be configured to generate a stimulation signal $V_{stim}$ that may be characterised by a set of parameters, and to transmit the stimulation signal $V_{stim}$ to one or more of the electrodes (12). For example, the stimulation module (16) may comprise a pulse generator having a current source (and/or voltage source) that generates electrical signals that have parameters specified by a user and/or the control module. In some variations, a pulse generator may form output pulses having specified amplitude ($V_a$), frequency ($V_f$) and/or pulse width or duration ($V_d$) values. Optionally, a pulse generator may generate a pulse sequence having two pulses or more pulses repeated with a duty cycle specified by a user and/or the control module, and the control module may adjust the pulse duty cycle in accordance with one or more properties of the acquired neural activity signals (e.g., any of the patterns or properties described herein).

The acquisition module (20) may comprise input ports $V_1$ and $V_2$ that are each connected to different electrodes (12) on the probe (11) and electrical circuits that are configured to measure the electric field variations of the local biopotentials or local field potentials (LFPs) based on the signals from the input ports $V_1$ and $V_2$. Electrical circuits of the acquisition module may comprise one or more processing units or processors (e.g., a CPU, and/or one or more field-programmable gate arrays, and/or one or more application-specific integrated circuits) that may be configured to perform computational operations, one or more memory elements, one or more amplifiers, one or more filters, and/or one or more analog-to-digital converters. As depicted in FIG. 1B, the acquisition module (20) may measure electric field variations by sensing changes in the electric potentials $V_1$ and $V_2$ (e.g., difference(s) between $V_1$ and $V_2$, or values of $V_1$ or $V_2$ as referenced to a common or ground electrode (17)) using a pre-amplifier and may amplify the changes (and/or any electric field variations) using an amplifier. The amplified output may be converted to a digital signal using an analog-to-digital converter, and the digital signal may be transmitted to the control module (18) for further analysis and processing. In some variations, the acquisition module (20) may comprise an acquisition processor that is configured to transform the acquired neural activity signals (e.g., LFPs) into spectral signals (e.g., spectral power values) that represent cerebral activity in the frequency domain (i.e., frequency-domain representation). For example, an acquisition processor of the acquisition module may be configured to carry out a Fourier Transform (e.g., a Fast-Fourier Transform or a Discrete-Fourier Transform) of the neural activity signals from input ports $V_1$ and $V_2$. The acquisition processor may comprise a general-purpose microprocessor that executes instructions from a software program to perform the frequency-domain signal transformation. Alternatively or additionally, the acquisition processor may comprise a digital signal processor (DSP) that has specialized electrical circuitry for performing the frequency-domain signal transformation. Alternatively or additionally, the acquisition processor may comprise an FPGA and/or ASIC configured for performing the frequency-domain signal transformation. Additionally, the acquisition processor(s) of the acquisition module (20) may be configured to calculate the power values of the neural activity signals in certain frequency bands of interest (e.g., the low-frequency band, alpha frequency band, beta frequency band, gamma frequency band, and/or any range of frequencies as may be desirable). In some variations, the acquisition processor may perform the power calculation in the time domain. The acquisition processor may comprise a band pass filter followed by a rectifier to perform the power calculation in the time domain. In some variations, the processor(s) of the acquisition module (20) may comprise an integral block and a derivative block (not illustrated) of the power values in order to highlight respectively slow and fast time changes of the power values. An integral or integration block may be configured to combine power values over time (e.g., by calculating an average value, which may be a moving average value) to help enhance slower changes or longer-term trends in power values. A derivative block may be configured to combine power values to help enhance faster or instantaneous changes in power values.

In some variations, the acquisition module (20) may comprise electrical circuitry that reduces noise and/or signal artifacts from the biopotential or LPF signals detected by the electrodes (12) on the probe (11). In one variation, the circuitry of the acquisition module may be configured to remove signal artifacts of a LPF signal from one electrode that may arise from electrical stimulation that is being delivered to the brain region through another electrode. Such circuitry allows the DBS system (10) to acquire neural activity signal data concurrently with the delivery of electrical stimulation (e.g., acquiring neural activity signal data while delivering electrical stimulation on the same electrode). For example, neural activity signal data may be acquired on a first electrode of a probe while electrical stimulation may be delivered on a second electrode of the same probe. The acquisition module (20) may comprise a low-gain pre-amplification stage to amplify the signal while preventing saturation and not-linear effects. The pre-amplification stage may be followed by an high-order low pass filter to suppress high frequency stimulation harmonics. The pre-amplified and filtered signal may then be amplified to match the ADC dynamics by an additional amplification stage. Additionally or alternatively, the acquisition module may include a low pass and/or high pass passive filter(s) before the pre-amplification stage to further suppress the stimulation artefact. In some variations, a single probe comprising one or more stimulation electrodes and one or more signal acquisition electrodes that are different from the stimulation electrodes and the acquisition module may be configured with circuitry that allows for the acquisition of neural activity signals concurrently with electrical stimulation. Alternatively or additionally, a single probe may comprise one or more electrodes that may each be configured to deliver electrical stimulation and acquire neural activity signals concurrently (e.g., the same probe is injecting current and measuring biopotentials simultaneously or sequentially). Additional variations of electrical circuitry that process acquired electrical signal data while simultaneously delivering electrical stimulation on the same probe are provided in U.S. Pat. No. 8,078,281, which is hereby incorporated by reference in its entirety.

Amplified neural activity signal data (that has been processed as described above, or not processed) may be transmitted via an output port $V_{out}$ to the control sub-system or module (18). The control module (18) may comprise a controller having one or more processors (e.g., microprocessors) and one or more memory elements in communication with the one or more processors. The processor(s) of the control module (18) may be configured to calculate the parameters of electrical stimulation based on user input and/or signal input from the acquisition module (20). In some variations, the control module (18) may be configured to calculate the power values of the neural activity signals in certain frequency bands of interest (e.g., the low-frequency band, alpha frequency band, beta frequency band, gamma frequency band, and/or any range of frequencies as may be desirable), and calculate the value of one or more electrical stimulation parameters based on the calculated power values of the frequency bands of interest. For example, the control module (18) may be configured to calculate stimulation pulse amplitude, duration, and/or frequency in accordance with the power values of the frequency bands of interest and/or the spectral content of the neural activity signals acquired by the acquisition module (20). The control module (18) may also comprise a memory bank or element that stores neural activity signals, stimulation parameters (e.g., previously selected or calculated parameter values), and/or instructions for adjusting or modifying the stimulation parameters based on neural activity signals and/or user commands. In a closed-loop aDBS system, the control module (18) may store tables or matrices that map characteristics or patterns of neural activity with various electrical stimulation parameters. The tables or matrices may represent one or more transform functions that translate or convert neural activity signals (and/or patterns) into stimulation parameter values so that the electrical stimulation delivered to the brain region is responsive (i.e., tailored or customized) to the disease or clinical state of a patient's brain. In some variations, when a tic is detected a specific set of stimulation parameters may be selected based on a look-up table. For example, the control module may comprise a look-up table including at least two stimulation configurations, one to be applied after the detection of a tic (or any symptom associated with TS) and one in absence of tics. Optionally, a look-up table may comprise a plurality of electrical stimulation parameter values or configurations that may be indexed by different patterns of neural activity signals. For example, a first pattern of neural activity signals may map to a first set of electrical stimulation parameter values, a second pattern of neural activity signals may map to a second set of electrical stimulation parameter values, and so on. The first pattern of neural activity signals may indicate that no tic is present and the second pattern of neural activity signals may indicate that a tic is in progress. When the control module or controller detects the first pattern of neural activity signals, a command signal may be transmitted to the pulse generator to generate electrical stimulation having the first set of electrical stimulation parameter values, and when the control module or controller detects the second pattern of neural activity signals, a command signal may be transmitted to the pulse generator to generate electrical stimulation having the second set of electrical stimulation parameter values. In some variations, the control module (18) may be configured to monitor neural activity signals from at least one electrode (e.g., an electrode on a single probe located at one region of the brain, and/or a combination or pattern of signals from a pre-determined grouping of electrodes on the same probe or across more than one probe, etc.) based on which at least one parameter $V_a$, $V_d$, $V_f$ of the stimulation signal $V_{stim}$ set by the stimulation module (16) has been modified.

Alternatively or additionally, the acquisition module (20) may transmit the frequency-domain transformed neural signal data and/or the time-domain neural signal data to the control module (18). The control module (18) may be configured to determine the power spectrum (i.e., one or more power values for one or more frequency bands) of the brain activity based on one or both of the frequency-domain and/or time-domain signals. Optionally, the mathematical operations of power calculation, integration and derivatives may be distributed between the hardware and/or electrical circuitry of the control module (18) and the acquisition module (20). In some variations, the control module and/or acquisition module may comprise an application-specific integrated circuit or ASIC having circuitry configured for efficient FFT analyses and calculations. While the processor(s) of the control module may be configured to calculate or determine the parameters of electrical stimulation, alternatively or additionally, in some variations, the acquisition module may comprise an acquisition processor that may be configured to calculate the parameters of electrical stimulation based on the acquired neural activity signals. For example, the acquisition processor may be configured to calculate the power values of the neural activity signals in certain frequency bands of interest (e.g., the low-frequency band, alpha frequency band, beta frequency band, gamma frequency band, and/or any range of frequencies as may be desirable), and calculate the value of one or more electrical stimulation parameters based on the calculated power values of the frequency bands of interest. For example, the acquisition processor may be configured to calculate stimulation pulse amplitude, duration, and/or frequency in accordance with the power values of the frequency bands of interest and/or the spectral content of the acquired neural activity signals.

The stimulation device to which the electrodes are connected (e.g., stimulation device (14)) may be implantable or may be configured to be externally coupled to the patient (e.g., a wearable device attached to a lanyard, band, apparel, etc.). For example, the stimulation device may be implanted below a patient's skin but outside of neural tissue, and in some variations, may be implanted along the external surface of the skull, or implanted under a patient's skin in the chest region (e.g., below the collarbone), or in the abdomen. The communication between the probe(s) and the stimulation device may be via one or more electrical wires, or may be wireless. The stimulation device may also comprise a battery or other power source that may be used to provide power to a pulse or function generator that provides electrical stimulation to the probe(s) and/or to provide power to the various sub-systems of the simulation device. The battery may be rechargeable, using induction mechanisms (e.g., via a pair of induction coils, one in the stimulation device and one in a power source) or by wire connection to a power source. Alternatively, the battery may not be rechargeable and may instead be replaced when expired or exhausted. For example, a rechargeable battery may be recharged daily, where each charging session lasts about 20 minutes, with a maximum current of 60 mA. The control module may monitor the charge level and/or the temperature of the battery while the battery is re-charging, and when the charge level and/or temperature reach a threshold level, the control module may issue a command to pause or stop charging the battery. For example, the control module may issue a command to a power management or battery management module pause or stop charging the battery if the battery has reached a charge level of at least 80% of full capacity (e.g., about 85% of capacity, about 90% of capacity, about 95% of capacity, about 100% of capacity, etc.) and/or if the battery temperature exceeds an upper temperature threshold (e.g., above which the battery may be damaged or otherwise compromised). In some variations, the stimulation device may comprise a data connection or link to a remote computer or server, and/or a handheld device (e.g., tablet, portable computing device, smartphone, and the like) which may optionally be connected or linked to a remote computer or server. For example, neural activity signals, electrical stimulation parameters, and/or other data may be transmitted from the stimulation device to a handheld device. The handheld device may transmit updates to the tables, matrices, and/or functions stored in the control module, user input or commands, and in some variations, may process or analyze the neural activity signals to derive electrical stimulation parameters and may transmit the calculated stimulation parameters to the stimulation device. The data connection or communication link may be wireless (e.g., where the stimulation device and the remote computer each have wireless transceivers) or may be a wired connection (e.g., where the stimulation device and the remote computer are connectable using a data bus or cable). For example, a wireless communication link may comprise a wireless transceiver that is configured to use a 2.4 GHz ISM band and 10 kbaud for receiving and transmitting programming commands, and 500 kbaud for transmitting physiological data as a digital modulation technique. The control module may control the wireless transceiver by means of a serial communication interface (SPI).

While the system described above and depicted in FIG. 1A comprises a single probe with multiple electrodes, other variations may comprise two or more probes, each with one or more electrodes. The probes may be configured to be implanted in different brain regions, and may each comprise electrodes with different functions. As described above, the electrodes may be stimulation electrodes only, measurement electrodes only, or may be stimulation and measurement electrodes. A single probe may have two or more of the electrode types described herein, or may have only electrodes of a single type.

Another variation of a stimulation device that may be included in a DBS system for the treatment of TS is depicted in FIG. 1C. Stimulation device (100) may comprise a stimulation module (102), an acquisition module (104), and a control module (106) in electrical communication with the stimulation module (102) and the acquisition module (104). The stimulation device (100) may also comprise a header interface (108) with one or more ports for connecting one or more probes, a coil (110) for inductive charging of the battery of the stimulation device, and an antenna (112) for wireless communication between the stimulation device (which may be implanted under the skin of a patient) and an external device (e.g., a handheld device). In some variations, the stimulation module (102), acquisition module (104) and control module (106) may be enclosed in a housing (107) while the header interface (108), coil (110), and antenna (112) may be located outside the housing (107), each enclosed within their own individual housings. Alternatively, the header interface, coil, and antenna may be enclosed in the housing (107).

In some variations, the stimulation module (102) may comprise a current controller (114), waveform generator (116), and a multiplexer (or multiplexer array) (118). The current controller (114) and the waveform generator (116)

may be in electrical communication with the control module (106) to receive signals representing electrical stimulation parameters for the generation of electrical stimulation. For example, the control module (106) may generate a signal containing electrical stimulation pulse amplitude values to the current controller (114) and a signal containing electrical stimulation pulse width and/or frequency values to the waveform generator (116). The control module (106) may also determine or calculate or otherwise select the electrode(s) through which the stimulation is to be delivered to brain region and transmit a signal to the multiplexer (118). Based upon the signal from the control module, the multiplexer (118) is configured to arrange the electrical connections between the waveform generator and the electrodes of the probes connected to the stimulation device via the header interface (108) so that the generated electrical stimulation signal is transmitted to the selected electrode(s). For example, the multiplexer (118) may be configured to arrange the connectivity between the waveform generator and the electrodes to have a monopolar stimulation configuration and/or a bipolar stimulation configuration. In a monopolar configuration, one or more electrodes may be connected to one or more active terminals (e.g., positive terminal(s), negative terminal(s)) of the waveform generator (with a return pad placed elsewhere on the patient). In a bipolar configuration, a first set of one or more electrodes may be connected to one or more active terminals of the waveform generator while a second set of one or more electrodes (e.g. distinct from the first set of electrodes) may be connected to one or more return terminals of the waveform generator. The stimulation module (102) may comprise any one or more of the stimulation module electrical circuitry described herein.

In some variations, the acquisition module (104) may comprise a sensing module (120), an acquisition processor (122), and a sensing module power regulation module (124) in communication with the acquisition processor and the sensing module. The sensing module (120) may be connected to the header interface (108), with the same or different probes to which the stimulation module (102) is connected. The sensing module (120) may comprise two recording channels that, after having filtered and amplified the LFP signals using one or more filters and/or amplifiers of the sensing module, may transmit them to the acquisition processor (122) for further signal analyses. The sensing module (120) may also comprise an array of multiplexers configured to electrically arrange the conductive paths of the electrodes so that the acquisition module is connected to the electrodes from which LFP data is to be acquired. After the LFP data is filtered by the sensing module (120), the LFPs may be converted into digital signals by an analog-to-digital converter of the acquisition processor (122). The acquisition processor may comprise circuitry configured to extract the spectral power value(s) of one or more frequency bands for each LFP signal and to calculate or determine a set of electrical stimulation parameters. In some variations, the power of one or more frequency bands of the acquired LFPs and the calculated set of electrical stimulation parameters may be transmitted to control module. For example, the acquisition processor may send physiologically-relevant parameters (e.g., the actual power value of the beta band, the power spectrum between 5 and 35 Hz, and the actual value of stimulation amplitude) to the control module. The acquisition processor (122) may also comprise circuitry configured to controls the array of multiplexers in the sensing module (120) to select the pairs of electrodes to perform the acquisition of the LFPs. For example, in a variation where the DBS system comprises a probe with eight electrodes (which may be implanted in one side of a patient brain), any combination of a pair of electrodes (e.g., two electrodes) selected from the eight electrodes may be selectable by the acquisition processor. The acquisition processor may comprise circuitry configured to control the gain of the two recording channels (i.e., used to measure the LPFs of the selected electrode pair), and may be configured to activate/deactivate the power regulation module (124) for providing a supply voltage to the sensing module (120). The sensing module power regulation module (124), once activated, may generate a supply voltage for the sensing module (120). The acquisition processor may optionally also select one out of four different gains for the recording channels. In some variations, the gain setting selection may be for one or both the channels, i.e. the channels have the same gain. The LFP signals may sampled by an analog-to-digital converter (ADC) included in the acquisition processor. In the variation depicted in FIG. 1C, a single ADC may be configured to sequentially sample the two channels, but in other variations, there may be two ADCs, one for each channel (i.e., electrode) recording.

The control module (106) may comprise a control module (main) processor (130), one or more memories (132), a RF chip or module (134) for managing data transmission, a rechargeable battery (136), a recharging and battery management circuit (138), a stimulation module power supply management module (140), a calibration or diagnosis module (142) for the stimulation module, and an impedance meter (144). The main processor (130) may comprise circuitry (e.g., a microcontroller or computing processing unit) configured to receive a set of electrical stimulation parameters and the temporal/frequency features of the LFP (e.g., power values of one or more frequency bands of the LFPs) from the acquisition module (104), and may store the stimulation parameters and/or the temporal/frequency features of the LFP in the memory (132). The memory (132), which may include one or more memory elements or memory banks, may be a non-volatile memory technology (e.g., flash memory, F-RAM, MRAM, etc.). For example, the memory (132) may comprise a 1 Mbit ferromagnetic memory element, and may be configured to store stimulation configurations and parameters, physiological parameters, patient-specific data (e.g., ID number and clinical data), and/or stimulation device-specific (i.e., IPG-specific) data (e.g., ID, serial number, model number, batch number, etc.). The RF module (134) may be in communication with the antenna (112) and configured to facilitate the reception and transmission of signals between the stimulation device and an external (e.g., handheld) device. For example, the RF module (134) may be coupled with a 2.4 GHz antenna to receive and transmit data. The RF module may be configured to notify the main processor (130) when a data packet is received from an external device, and communicate its content upon request of by the main processor (130). The recharging and battery management circuit (138) may comprise an inductive link via the coil (110) for recharging the battery (136), and may have circuitry configure to monitor the recharging process. For example, the battery management circuit or module (138) may be linked to the inductive coil (110) and to the rechargeable battery (136). This management circuit (138) may be configured to detect a current flow (i.e., from the coil to the battery), and may transmit the status of the current flow to the main processor (130). The management circuit (138) may also be configured to generate a voltage supply for the discrete components of the control module (106), for example, the main processor (130). Optionally, the management circuit (138) may be configured to the temperature of the battery and/or recharging link or coil, and transmit a signal indicating a temperature increase (i.e., caused by the recharging process) to the main processor (130). The main processor (130) may optionally be configured to send command signals to the stimulation module power supply management module (140) to activate and/or deactivate the power supply to the stimulation module (102), and may also be configured to control the stimulation module by setting the stimulation frequency, the stimulation amplitude, and/or the stimulation pulse width of the electrical stimulation, as described above. In addition, the main processor (130) may be in communication with the calibration or diagnosis module (142) in order to monitor the function of the stimulation module, and/or the impedance meter (144) in order to monitor the contact between the electrode(s) and target tissue, and/or the multiplexer (118) of the stimulation module (102) to select the electrodes for the delivery of electrical stimulation. The calibration or diagnosis module may comprise circuitry configured to check the functioning of the stimulation module and to detect whether the stimulation module generating electrical stimulation current as specified by the control and/or acquisition modules. The impedance meter (144) may be configured to measure the impedance of each electrode of each of the probes in order to evaluate the quality of the electrode-tissue contact interface.

FIG. 2A depicts one variation of a probe comprising one or more electrodes that may be used with any of the DBS systems described herein. Probe (200) may comprise a distal portion (202), a proximal portion (204), a tubular portion (203) extending between the distal and proximal portions. The one or more electrodes (206) are located on the distal portion (202) and one or more connector contacts (208) are located on the proximal portion (204). The probe (200) may comprise one or more wires (not shown) located within a longitudinal lumen of the tubular portion (203) that electrically connects the electrodes (206) with the connector contacts (208). A probe (200) may comprise any number of electrodes. In this variation, the probe has four electrodes and four connector contacts each of which correspond with one of the four electrodes. The electrodes (206) and/or connector contacts (208) may be made of any conductive material, for example, a metal or metal alloy (e.g., copper, gold, platinum iridium, etc.), and the tubular portion (203) may be made of any electrically insulating material (e.g., pellethane, ethylene tetrafluoroethylene (ETFE), polytetrafluoroethylene (PTFE), rubber, etc.). Each of the four electrodes and/or four connector contacts may be separated by an insulating material such as pellethane, ETFE, PTFE, and the like. The electrodes and/or connector contacts may have any shape, for example, may be disk-shaped, ring-shaped (i.e., partially or fully circumscribing the circumference of the tubular portion), circular, rectangular, ovoid, etc. The electrodes (206) may be ring-shaped, having a width from about 0/75 mm to about 2.5 mm, e.g., about 1.5 mm, having a separation distance from about 0.25 mm to about 1.25 mm, e.g., about 0.5 mm, wide ring of pellethane. The connector contacts (208) may be ring-shaped, having a width from about 1.5 mm to about 3 mm, e.g., about 2.3 mm, having a separation distance from about 1.5 mm to about 3 mm, e.g., about 2 mm, wide ring of pellethane. The length of the probe (200) may be selected depending on the depth and/or location of the target brain region, and in this variation, the length may be from about 25 cm to about 60 cm, e.g., about 40 cm.

In some variations, a probe may be connectable to a probe extension, which may electrically connect the probe electrodes to the stimulation device. The probe extension may be detachably attached to the probe, allowing the probe extension to be exchanged without changing the location of the probe within a patient's brain. FIG. 2B depicts one variation of a probe extension that may be used (optionally) with the probe of FIG. 2A. The probe is electrically connected to the stimulation device (e.g., implantable pulse generator) via the probe extension via a port of the header interface. A probe extension (210) may have a distal portion (212) having a connector block (213) with a receptacle housing (214) enclosing one or more conductive contacts (216), a proximal portion (218) having one or more stimulation device connector contacts (220). Each of the conductive contacts (216) in the receptacle housing may be connected to a corresponding stimulation device connector contact via one or more wires located within an elongated body (222) between the proximal portion (218) and the distal portion (212). A probe extension (210) may comprise any number of conductive contacts (216) which may correspond with the number of electrodes in the probe. The number of conductive contacts of the probe extension may be the same as, or greater than, the number of electrodes on the probe to which the probe extension is connected. For example, in this variation, the probe may have four electrodes and four connector contacts, and the probe extension may have four conductive contacts but eight stimulation device connector contacts. The distal portion of the probe may be implantable into the target brain region, while the proximal portion of the probe may extend outside of the brain tissue and connect with a distal portion of a probe extension. The receptacle housing of the probe extension may be configured to retain the proximal portion of the probe such that the connector contacts of the probe electrically connect with the conductive contacts of the probe extension such that the electrodes at the distal portion of the probe are electrically coupled to the stimulation device connector contacts a the proximal portion of the probe extension. In use, the probe proximal portion (204) may be inserted into the receptacle housing (214) via a distal-most opening (215) of the housing (214), such that connector contacts (208) abut the conductive contacts (216). The stimulation device connector contacts (220) may be configured to be coupled to a port or connector of the stimulation device (e.g., a header interface), as described above. In some variations, the receptacle housing may comprise an attachment mechanism to engage or retain the proximal portion of the probe within the receptacle housing, for example, a set screw, clamp, and/or clips, and/or by friction-fit, and/or by screw-fit. The receptacle housing (214) may comprise an opening sized and shaped for a set screw (217) which may be used to secure a probe that has been inserted into the distal opening (215) of the receptacle housing. Optionally, the probe extension may comprise a connector sleeve or boot (224) comprising an electrically insulating material that is disposed over at least a portion of the receptacle housing (214) to help electrically isolate the connector contacts of the probe and the conductive contacts of the probe extension from surrounding tissue. For example, a connector boot (224) may be made of a plastic or other electrically-insulating material and shaped as a sleeve sized to wrap around the receptacle housing to help seal or enclose the juncture between the probe and the lead extension. The boot (224) may have a thickness from about 0.75 mm to about 2 mm, e.g., about 1.25 mm, to help electrically isolate the contacts of the probe and/or the probe extension from the surrounding tissue or skin. The elongated body (222) of the probe extension (200) may have a constant diameter between the distal portion (212) and the proximal portion (218), or may have a varying diameter along its length. For example, the diameter of a segment of the elongated body (e.g., a transition segment) may be larger (e.g., thicker) where that segment is intended to be located at the interface between brain tissue and the skull or skin. The increased diameter of the transition segment may be due to an additional silicone overmold or additional flexible coating(s) (e.g., ethylene tetrafluoroethylene (ETFE), polytetrafluoroethylene (PTFE) and the like) over the length of the transition segment. This may help reduce excessive twisting, torqueing, and/or bending of the wires within the elongated body of the probe extension, thereby reducing the mechanical wear on the wires and/or helping to prolong the usable life of the probe extension. The length of the transition segment (226) may be from about 10 cm to about 20 cm, e.g., about 12 cm, about 15.6 cm, about 18 cm, etc. The overall length of the probe extension may vary depending on the distance and/or relative location of the probe implantation site in the target brain region and the location where the stimulation device is implanted (e.g., in a chest or abdominal region). In some variations, the overall length of the probe extension may be from about 300 mm to about 1000 mm, e.g., about 450 mm, about 500 mm, about 700 mm, etc.

While the probe of FIG. 2A is configured for use with the probe extension of FIG. 2B, it should be understood that in some variations, a probe may be configured to be directly connected to a stimulation device. For example, a probe may comprise a proximal portion that is more flexible than the distal portion (which may be implantable into the target brain region), where the proximal portion may have a length that extends from the target brain region to the location where the stimulation device is implanted (e.g., in the chest region or abdomen region).

Methods

Described herein are methods of closed-loop adaptive stimulation for the treatment of TS that may be used with any of the DBS systems described herein. The methods may comprise monitoring neural activity signals acquired by one or more probes in the presence or absence of electrical stimulation, determining whether the neural activity signals have one or more characteristics or patterns indicative of one or more symptoms of TS (e.g., a tic), and applying electrical stimulation to prevent or mitigate the symptom(s). Some methods may comprise identifying neural activity signals that predict the onset or occurrence of a TS symptom and applying electrical stimulation to prevent TS symptom onset. Alternatively, or additionally, methods may comprise identifying neural activity signals that indicate that the TS symptom is in progress (i.e., has begun or is ongoing) and applying electrical stimulation to reduce the duration and/or severity of the TS symptom. In some variations, applying electrical stimulation in response to a detected characteristic or pattern of neural activity comprises adjusting the parameters of ongoing electrical stimulation to modulate the signalling between neurons that cause the behaviours associated with TS. Adjusting the parameters of electrical stimulation may include, but are not limited to adjusting the amplitude, pulse width, frequency, duty cycle, etc.

One method for aDBS for the treatment of TS may comprise acquiring electrical neural activity signals using an implanted electrode, determining a power value of the acquired signals in a first frequency band, determining whether a decrease in the power value in the first frequency band (relative to a baseline value) is followed by an increase in the power value of the first frequency band (relative to the baseline value), and if this condition is met, modifying the electrical stimulation delivered to the brain region according to the acquired neural activity signals. Optionally, some methods may comprise determining a second power value of the acquired signals in a second frequency band, determining whether the second power value increases at the same time that the first power decreases, and if this condition is met, modifying the electrical stimulation delivered to the brain region according to the acquired neural activity signals. Some methods may comprise monitoring the power values in either or both of the first and second frequency bands. The acquisition of neural activity signals and/or monitoring of power values (or any activity signal patterns or characteristics) may occur in the presence or absence of electrical stimulation. That is, signal acquisition and/or monitoring may occur simultaneously or concurrently with electrical stimulation. In some variations, an aDBS system may monitor the time duration of power value variations and fluctuations as part of a method for determining the onset or occurrence of a symptom associated with TS. For example, the time duration of a particular power value change (e.g., an increase in the power value and/or a decrease in the power value) may range from about 100 ms to about 1000 ms, e.g., about 200 ms, about 250 ms, about 400 ms, about 500 ms or more, etc.

One variation may comprise monitoring the power values of one or more frequency bands of the acquired neural activity signals, and adjusting electrical stimulation parameters based on at least one variation of the monitored power values. Power variations in certain frequency bands may correlate with one or more symptoms of TS, and may, for example, provide an indication of an upcoming tic (and/or a tic that is currently in-progress). Without wishing to be bound by theory, there may be a correlation between certain features or patterns of neural activity signals (e.g., LPFs) and the various symptoms of the TS. For example, there may be a relationship between certain frequency bands in the frequency spectrum (e.g., sets of spectral power values) of the neural activity signals and certain neural symptoms. For example, oscillatory rhythms of acquired LPFs in certain frequency bands may correlate with the symptomatic state of the patient. Examples of frequency bands that may be monitored in any of the methods described herein include, but are not limited to, low frequencies (from about 2 Hz to about 7 Hz), the alpha band (from about 8 Hz to about 12 Hz), the beta band (low beta: from about 12 Hz to about 20 Hz, high beta: from about 20 Hz to about 35 Hz), the gamma band (from about 60 Hz to about 80 Hz) and high frequencies (from about 250 Hz to about 350 Hz). In some examples, LFP signals having certain profiles or patterns in the low-frequency band (from about 2 Hz to about 7 Hz) and/or the alpha band (from about 8 Hz to about 12 Hz) may be correlated with the symptomatic state of a TS patient. LFP signals in these frequency bands may be modulated by DBS to help improve TS symptoms.

The patterns or characteristics indicative of a symptom of TS may vary depending on the particular disease state or condition of the patient, and/or whether electrical stimulation is being applied at the time the neural activity signals are acquired. For example, in the presence or absence of electrical stimulation to a brain region, a pattern of neural activity in that brain region that may be indicative of a tic (e.g., at or before tic onset and/or during a tic) may include a decrease in the power value of a frequency band (e.g., the alpha band) for a first predetermined period of time and an increase in the power value of that frequency band for a second predetermined period of time after the first predetermined period of time. When an aDBS system detects or recognizes this pattern in the acquired neural activity signal, it may adjust or modify parameters of the electrical stimulation according to a set of stimulation parameters that corresponds with the detected or recognized pattern, where delivery of the adjusted stimulation to that brain region may help to prevent and/or alleviate the tic. In some variations, when a tic is detected, the frequency and/or pulse width of the electrical stimulation applied prior to the detection of the tic may be reduced by about 50% or more. The predetermined period of time may range from about 100 ms to about 400 ms, e.g., about 200 ms, about 250 ms. Optionally, the neural activity pattern that indicates a tic in the absence of electrical stimulation may include absolute or relative increases in the power values. The increases may be represented relative to a baseline value (e.g., a percentage increase over a baseline power value, a multiplicative factor over a baseline power value, etc.) where the baseline value is measured in the absence of a TS symptom. For example, the first frequency band power value increase may be from about 15% to about 40% (e.g., about 30%) over a baseline power value of the first frequency band, while the second frequency band power value increase may be from about 20% to about 50% (e.g., about 40%) over a baseline power value of the second frequency band. Optionally, the neural activity pattern that indicates a tic in the presence of electrical stimulation may include absolute or relative decreases and/or increases in the power values. The decreases and/or increases may be represented relative to a baseline value (e.g., a percentage increase over a baseline power value, a multiplicative factor over a baseline power value, etc.). For example, the frequency band power value decrease may be from about −50% to about −10% (e.g., about −20%) below a baseline power value of the frequency band, while the frequency band power value increase may be from about 50% to about 200% (e.g., about 150%) over the baseline power value of the frequency band.

The systems and methods described herein may measure neural activity signals and/or apply electrical stimulation to one or more brain regions to alleviate the systems of TS. Brain regions that have been found to underlie some of the symptoms of TS may include, but are not limited to, the ventro-oralis internus/centromedian nucleus-parafascicular complex of the thalamus (Vo/CM-Pf) region of the thalamus, posterior portion of the ventralis oralis (VOP), medial thalamus, globus pallidus internus (GPi), globus palidus externa (GPe), subthalamic nucleus (STN), intralaminar nucleus (ILN) of the thalamus, nucleus acumbens (NA), and/or anterior limb of the internal capsule (ALIC) region. While the variations described and depicted herein are in the context of implanting stimulation probes in the Vo/CM-Pf region of the thalamus, it should be understood that in other variations, stimulation probes may be implanted in one or more brain regions described above. In some variations, stimulation probes may be implanted in both hemispheres brain regions for bilateral stimulation.

The one or more brain regions selected for aDBS system implantation, neural activity monitoring and modulation may depend on the different symptoms and/or comorbidities that a clinician wishes to address. In TS, examples of comorbidities may include, but are not limited to, one or more of vocal tics, motor tics, attention deficit hyperactivity disorder, obsessive compulsive disorder, rage attacks, sleep issues, depression, migraines, and/or physical complications directly from violent motor tics (e.g., cervical myelopathy, arterial dissection, and/or stroke). For example, stimulation probe(s) may be implanted in the thalamus to address or treat motor and/or phonic tics. In a subset of patients where stimulation of the thalamus may cause comorbidities such as depression, dysarthria, nausea, and the like, stimulation probe(s) may instead be implanted in the anteroventral globus pallidus internus, which may help reduce motor, vocal and phonic tics, while causing fewer comorbidities (and/or reducing the severity and/or intensity of comorbidities). Alternatively, stimulation of the anterior limb of the internal capsule/nucleus accumbens may address or treat motor and/or phonic tics while reducing comorbidities such as obsessive-compulsive disorder. aDBS may comprise applying modifying or adjusting stimulation parameters upon the detection of neural activity patterns that are correlated with any of the comorbidities or symptoms listed above. In the case where aDBS comprises continuous electrical stimulation having baseline parameter values and/or characteristics, these parameters values may be modified or adjusted to a different set of values to address TS symptoms or comorbidities, and optionally, when the system has detected that the TS symptoms have been prevented and/or mitigated, the parameters of electrical stimulation may be reverted back to their baseline values.

Figure 4:
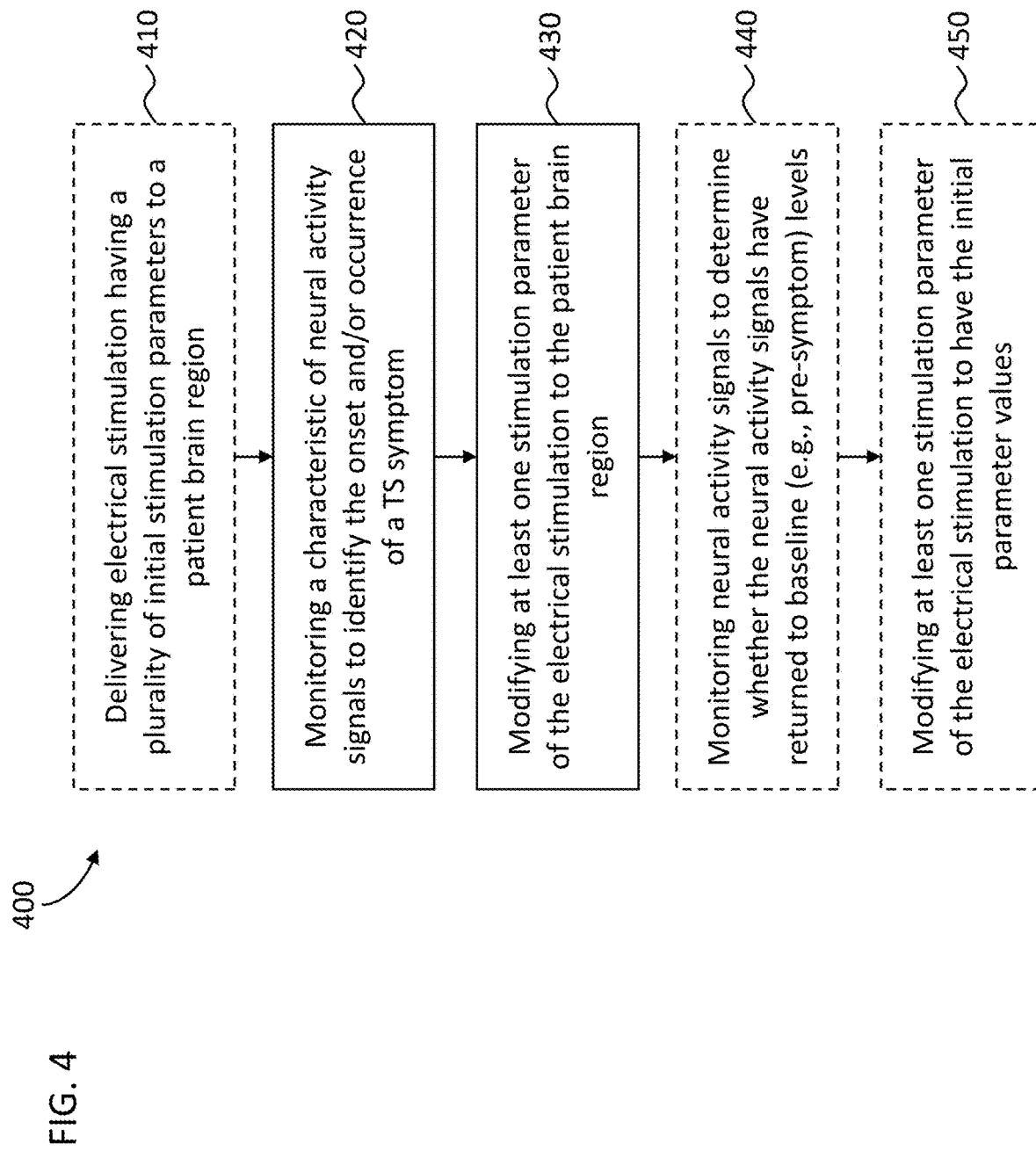
FIG. 4 depicts a flowchart representation of one variation of a method for treating Tourette Syndrome.

FIG. 4 depicts one variation of a method (400) for closed-loop, aDBS for the treatment of TS. The method (400) may comprise monitoring (420) a characteristic or pattern of the neural activity signals (e.g., LFPs) to identify the onset of involuntary movements (motor tic) or utterances (phonic tic) during the optional delivery (410) of electrical stimulation. The baseline or initial parameters of the electrical stimulation (e.g., pulse frequency $V_f$, duration $V_d$, amplitude $V_a$, etc.) delivered prior to an involuntary movement or utterance (or any TS symptom) may be customized or tailored to the patient (e.g., the parameters of the electrical stimulation have been previously confirmed to have a beneficial therapeutic effect and/or a desired or preferred patient outcome). The electrical stimulation may be continuously applied to the patient and the system may be configured to deliver electrical stimulation and measure LFPs simultaneously. In other variations, characteristics or patterns of neural activity signals may be monitored without the simultaneous delivery of electrical stimulation. In some variations, monitoring (420) a characteristic of neural activity that may be associated with the onset and/or occurrence of a TS symptom may comprise monitoring changes in a spectral power value recorded LFPs. If the aDBS system detects or identifies any characteristics or pattern of the neural activity signals (e.g., LFPs) that indicates the onset and/or occurrence of TS symptoms, method (400) may comprise modifying (430) at least one stimulation parameter (e.g., $V_a$, $V_d$, $V_f$) of the electrical stimulation to the patient in order to suppress the tic. After changing at least one stimulation parameter, method (400) may optionally comprise monitoring (440) the neural activity signals (e.g., LFPs) to determine whether the neural activity signals have returned to baseline levels (i.e., no longer contains characteristics or patterns linked to TS symptoms), and if so, method (400) may optionally comprise modifying (450) at least one stimulation parameter (e.g., $V_a$, $V_d$, $V_f$) of the electrical stimulation to the patient to have the initial parameter values (i.e., parameter values before a tic was detected). Monitoring (440) LFPs to determine whether they have returned to baseline levels may comprise, for example, determining whether the changes in the spectral power value(s) that are indicative of an onset and/or occurrence of a TS symptom have been "reset" to the spectral power value(s) prior to the onset of the symptom. Alternatively or additionally, the modifications to the at least one stimulation parameter may be time-limited and last for a predetermined period of time before reverting back to the original stimulation parameter(s). For example, the predetermined period of time may be from about 100 ms to about 1000 ms, e.g. 200 ms or more, about 250 ms or more, about 400 ms or more, about 500 ms or more, after which the stimulation parameter(s) may be reverted back to previous values and/or settings. In some variations, the stimulation signal duration $V_d$ (i.e., pulse width) and the stimulation signal frequency $V_f$ may be reduced to help suppress the involuntary movement. For example, the stimulation signal duration $V_d$ may be reduced from a baseline value (e.g., about 60 us to about 120 µs) to a duration value that is at least 50% less than the baseline value of $V_d$. (e.g., from about 10 µs to about 30 µs), and the stimulation signal frequency $V_f$ may be reduced from a baseline value (e.g., about 130 Hz or more) to a frequency that is at least 50% less than the baseline value of $V_f$ (e.g., between about 30 Hz and 35 Hz).

The characteristics or patterns of neural activity signals (e.g., LFPs) that indicate the onset of involuntary movements (motor tic), utterances (phonic tic), and/or any symptoms associated with TS may vary depending on the patient's disease condition, the brain region within with the probe is implanted, the relative orientation of the probe in the brain region, and/or whether or not the LFPs are measured in the presence or absence of electrical stimulation. Characteristics of neural activity signals may include, but are not limited to, the frequency content or spectra of the activity signals, cross-correlation of the activity signals, cross-power spectrum, phase-amplitude coupling, or more generally, relative timing characteristics of neural activity between two brain regions, action potential timing and density/frequency, and/or any deviations or variations from baseline levels of activity. Optionally, characteristics of neural activity signals may include cross-correlation, cross-power spectrum, phase-amplitude coupling across multiple data channels and/or recordings from multiple electrodes and/or multiple probes. In some variations, an aDBS system may be configured to detect changes or variations in the frequency spectral content of neural activity signals to determine the onset or occurrence of a tic. Certain frequency bands may contain data pertaining to symptoms of TS. For example, the amount of low-frequency neural activity and/or alpha band frequency neural activity, and/or the relative timing between fluctuations in these two frequency bands, may provide indicators of TS symptoms. Additional examples of characteristics or patterns of neural activity signals (e.g., LFPs) that indicate the onset of involuntary movements (motor tic), utterances (phonic tic), and/or any symptoms associated with TS are described below.

Figure 5:
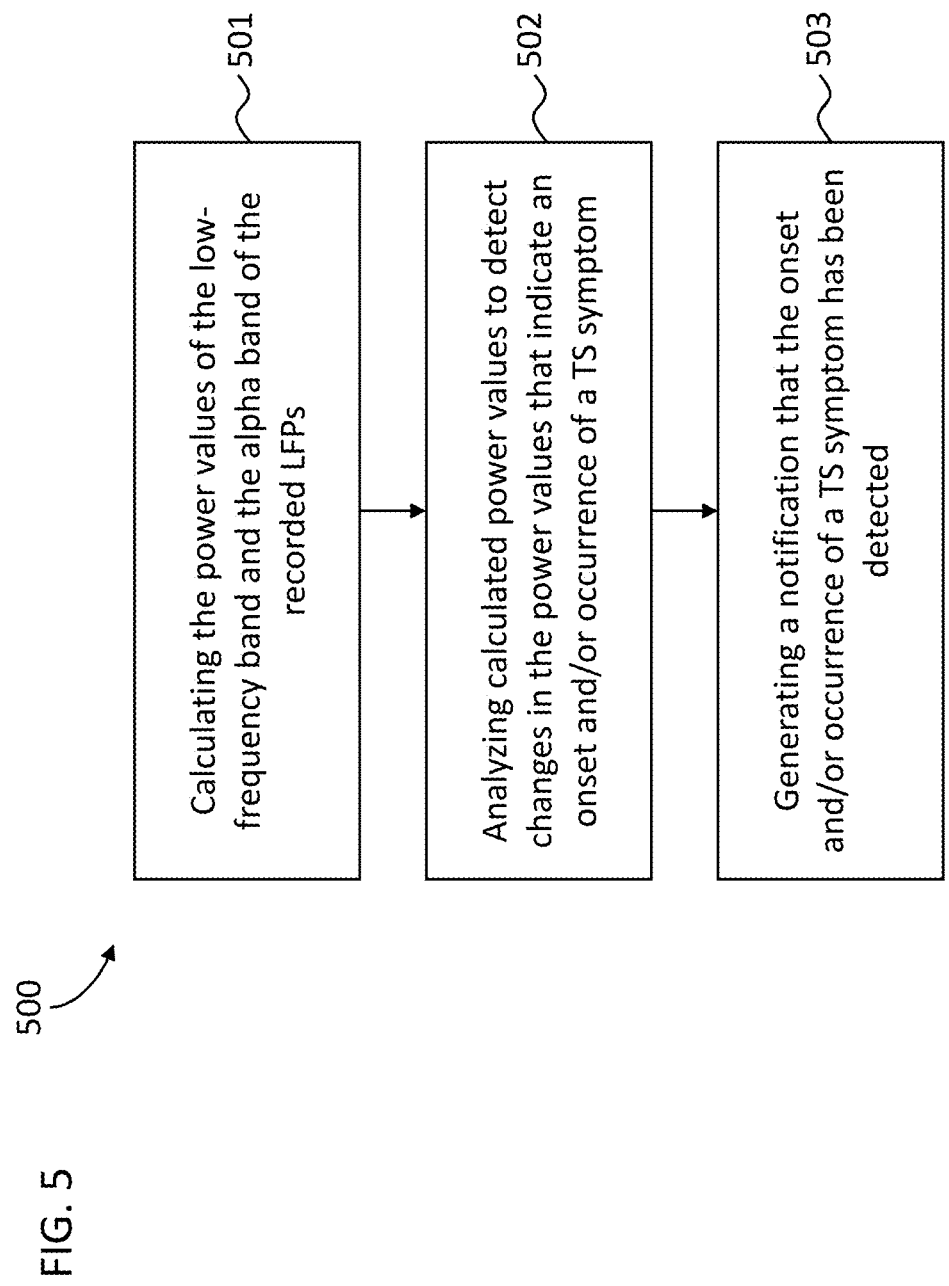
FIG. 5 depicts a flowchart representation of one variation of a method for monitoring a characteristic of neural activity signals for detecting the onset of motor and/or phonic tics.

One variation of a method (500) for monitoring patterns of neural activity by monitoring spectral content of LFPs is depicted in FIG. 5. Monitoring changes in the spectral power LFP signals may comprise extracting or calculating (501) the power values (i.e., spectral power values) of the low-frequency band and alpha band of the recorded LFPs. In some variations, the power values for the low-frequency and the alpha bands may be extracted by applying a band pass filter (e.g., one for the low-frequency band, about 2-7 Hz, and one for the alpha band about 8-12 Hz) to the acquired LFP signals, followed by a rectifier, followed by an average filter that averages changes over a time window. For example, a moving average filter having a time window width $t_{window}$ allows the observation of low-frequency and alpha changes in LFP signals over a $t_{window}$ duration window, with a $t_{delay}$ delay, where $t_{window}$ and $t_{delay}$ may be from about 50 ms to about 400 ms (e.g., about 100 ms or about 250 ms), and where $t_{delay}$ is the half of the $t_{window}$. The method (500) may comprise analyzing (502) the extracted (and optionally averaged) power values in order to detect changes which may announce the onset of a motor and/or phonic tic (or any TS symptom). For example, a pattern of neural activity that may indicate the onset of a tic (e.g., in the variation where the probe of the aDBS system is implanted in the Vo-Cm/Pf region) may comprise a decrease in the spectral power value of the alpha band (e.g., by at least 20% from a baseline value) for a first specified time interval (e.g., about 250 ms, the decrease lasts for about 250 ms or more) and an increase (e.g., by at least 150% from a baseline value) in the spectral power value of either one or both of the alpha band and the low frequency power band. If the changes in the power values that indicate the onset of motor and/or phonic tic have been detected (e.g., the conditions described above have been met), the method (500) may comprise generating an indication or notification (503) that the occurrence or onset of a symptom has been detected. In some variations, analyzing (502) the extracted power values may comprise detecting a decrease in the spectral power value of the alpha band by at least about 20% from a baseline value (e.g., the power value of the alpha band during the baseline phase) for a predetermined time period (e.g., about 250 ms or more) followed by an increase in the power value of the alpha band for another predetermined time period (e.g., about 250 ms or more), where the increase may be at least 2.5 times greater than its baseline value (e.g., about 5 times).

Optionally, the patterns or conditions that indicate the onset of a TS symptom may also specify time duration ranges for each of the power value increases or decreases. While in some variations, the duration of any power band increase or decrease may be at least 250 ms or more, in other variations, the duration of power band increases or decreases may be from about 100 ms to about 1000 ms, e.g., about 150 ms, about 200 ms, about 300 ms, about 325 ms, about 400 ms, about 500 ms, about 650 ms, etc.

In variations where monitoring patterns of neural activity indicative of TS symptoms comprise detecting activity patterns where the power value of the low-frequency band increases after the power value of the alpha band decreases, monitoring (140) the neural activity signals to determine whether the activity signals have returned to baseline levels may comprise determining whether the power value of the low-frequency band has decreased from its peak value (e.g., of about 150% of the baseline value, power value during the movement phase or in the presence or duration of a symptom or tic event). When the power value of the low-frequency has dropped to a threshold value (e.g., about +50% of its value in the baseline phase, about −50% of its peak value during the movement phase), the method may comprise modifying (150) at least one stimulation parameter (e.g., $V_a$, $V_d$, $V_f$) of the electrical stimulation to the patient to have the initial or baseline parameter values (i.e., parameter values before a tic or TS symptom was detected).

As indicated previously, any of the methods described herein may be performed in the absence or presence of electrical stimulation. That is, the methods of FIGS. 4 and 5 may be performed concurrently with the delivery of electrical stimulation (e.g., to the same brain region from which LFP signals are being acquired), and/or may be performed in alternating or sequential fashion with the delivery of electrical stimulation (e.g., LFP signals recorded during an acquisition phase, electrical stimulation delivered during a stimulation phase that occurs after the acquisition phase with little or no overlap, etc.), and/or may performed in a desired combination of concurrent or sequential fashion (e.g., LFP signals recorded during an acquisition phase, electrical stimulation delivered during a stimulation phase that occurs after the acquisition phase with little or no overlap, LFP signals recorded and electrical stimulation delivered simultaneously or concurrently in a combined acquisition-stimulation phase, etc.). The electrical stimulation waveforms may be in the frequency range from about 100 Hz to about 130 Hz, having pulse amplitudes from about 2 V to about 5 V amplitude range, and/or having pulse widths from about 60 μs to about 120 μs.

EXAMPLES

Described below are examples of patterns or characteristics of neural activity signals that indicate the onset and/or occurrence of a TS symptom (e.g., a tic). The patterns or characteristics described below may be used in any of the methods described herein for monitoring neural activity signals (e.g., LFPs) to determine whether electrical stimulation parameters should be adapted to prevent or otherwise mitigate a TS symptom. In some patients with motor or phonic tics, LFP recordings have shown two main oscillatory activity changes during tics, one in the low-frequency band and one in the alpha band. Experiments have shown that for some patients, low-frequency power values increase from baseline during a movement phase (i.e., the time duration of the tic) and a recovery phase (i.e., a time period or interval just after the tic). The power value of the alpha frequency band may also increase from baseline during the movement phase, and may show a desynchronization in the pre-movement phase (i.e., a time period or interval just before the tic onset); that is, a slight and short decrease of the power value prior to the onset of the tic. In some variations, a pattern of LFP activity that may be indicative of a TS symptom my comprise a decrease in the alpha band power value of at least 20% (i.e., relative to the alpha band power value in the baseline phase) for a first predetermined time period and a subsequent increase in the alpha band power value of at least 2.5 times greater (e.g., about 150% greater) than its baseline value for a second predetermined time period. Alternatively or additionally, a pattern of LFP activity that may be indicative of a TS symptom may comprise a decrease in the alpha band power value of at least 20% (i.e., relative to the alpha band power value in the baseline phase) for a first predetermined time period and a subsequent increase in the low-frequency band power value of at least 2.5 times greater (e.g., about 150% greater) than the low-frequency band power baseline value for a second predetermined time period. The first and second predetermined time periods may be the same or different, and may range from about 100 ms to about 1000 ms. For example, the first predetermined time period where the alpha-band power value is reduced may be about 250 ms or more.

Figure 3A:
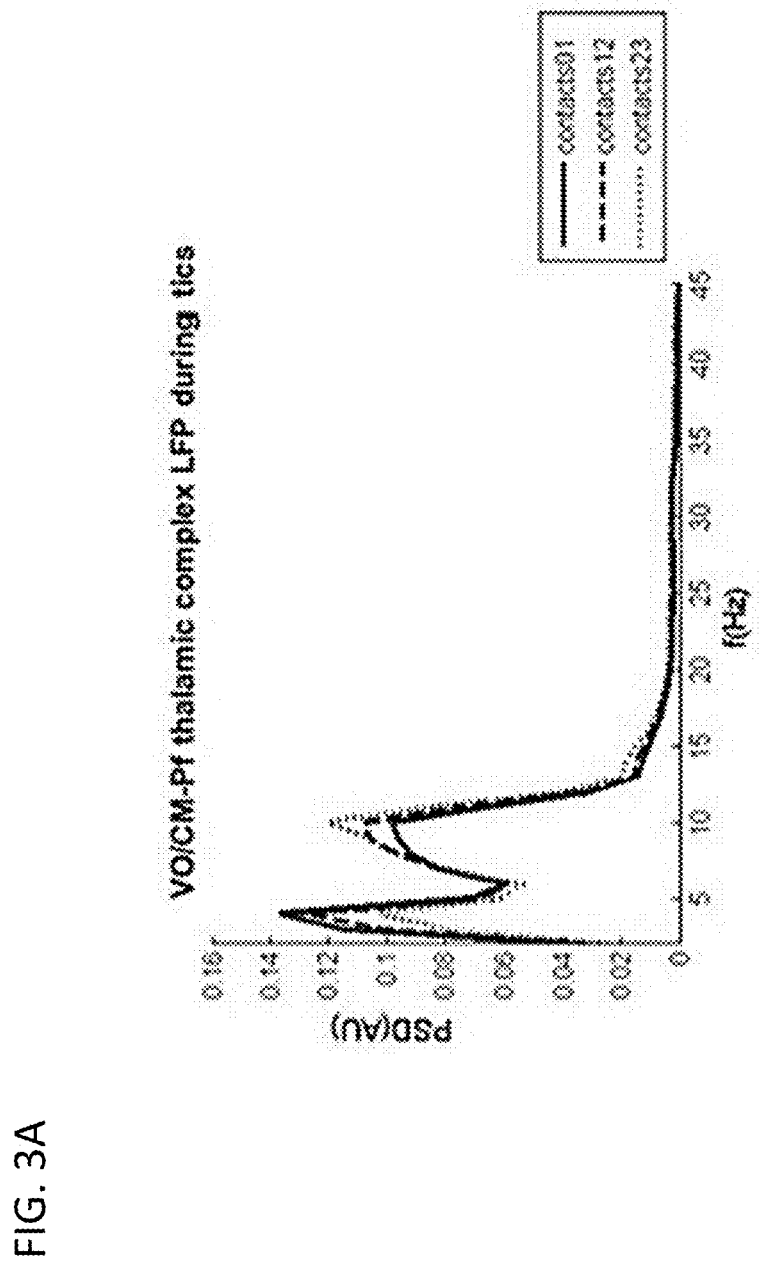
FIGS. 3A-3C are diagrams showing experimental neural activity data (LFP oscillations) recorded in the Vo/CM-Pf brain region by a probe having four electrode contacts (electrode contacts 0-3) during involuntary movements of a patient affected by TS.
Figure 3B:
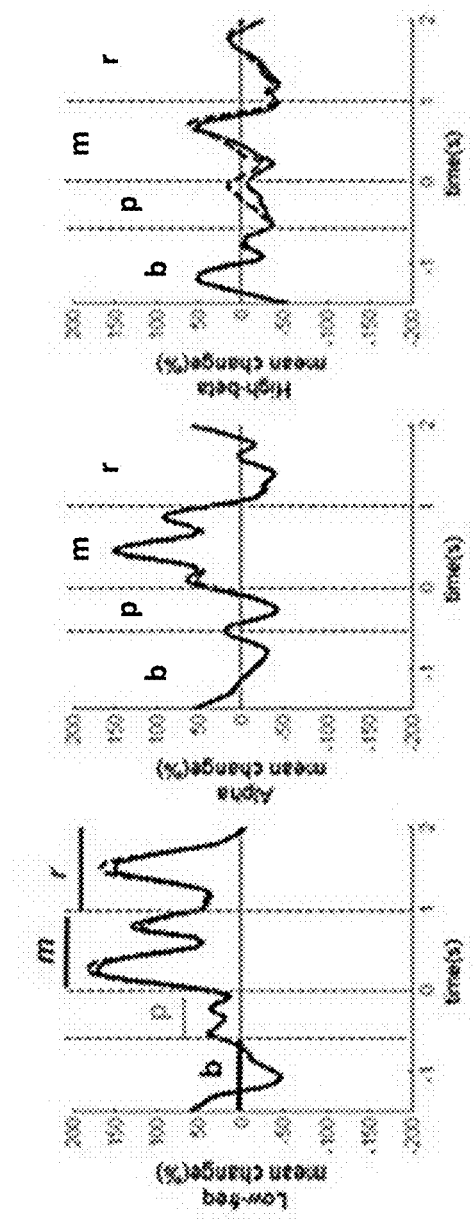
Figure 3C:
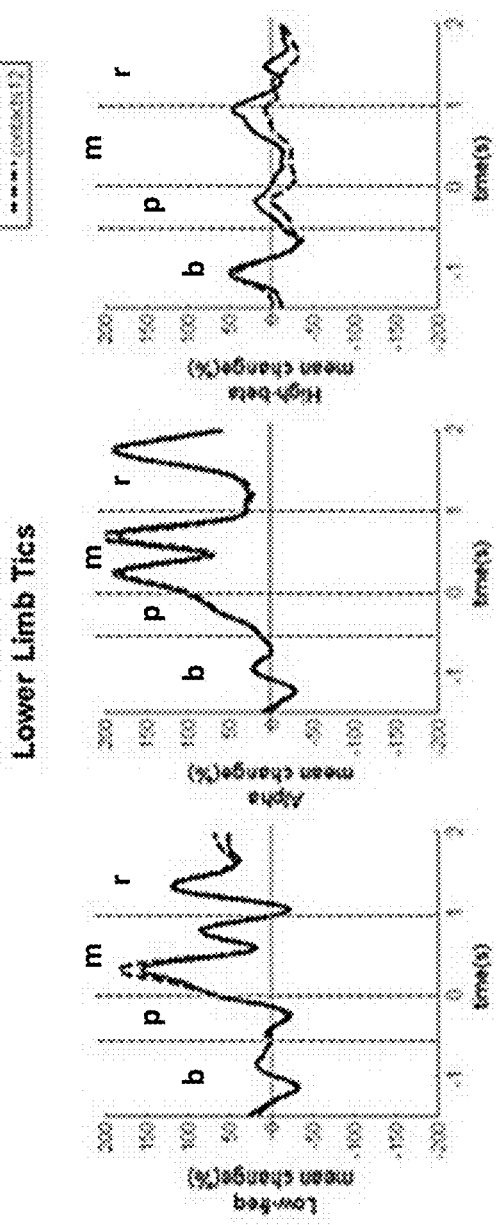

FIGS. 3A-3C depict data plots that represent neural activity signals (LFPs) measuring during an experiment where a probe having four recording electrodes (e.g., electrode 0, electrode 1, electrode 2, electrode 3) was implanted in the Vo/CM-Pf region of a patient's brain. The recording electrodes may be linearly arranged along the length of the probe, for example, as schematically depicted in FIG. 1A. The plots show Vo/CM-Pf LFP oscillations recorded during involuntary movements in one patient who showed severe motor tics, both on the upper and the lower limbs. FIG. 3A depicts the power spectrum of the LFPs recorded from a first electrodes configuration (black solid line), a second electrodes configuration (dashed black line), and a third electrodes configuration (dotted line) during motor tics. In the first electrodes configuration, the LFPs are recorded over electrode 0 and electrode 1, in the second electrodes configuration, the LFPs are recorded over electrode 1 and electrode 2, and in the third electrodes configuration, the LFPs are recorded over electrode 2 and 3. The x-axis represents frequency (Hz) and the y-axis represents the normalized power spectral density (PSD; arbitrary unit). FIG. 3B depicts LFP power modulations for the low-frequency (left), alpha (middle), and high-beta frequency (right) bands recorded during upper limb tics from a pair of electrodes (i.e., the first electrode and second electrode), averaged across all observed tics. Power modulations are expressed as percentage change from the baseline phase and were estimated from 1.5 s before the movement onset to 2 s after the movement onset. The four movement-related phases or intervals are: baseline (b), pre-movement (p), movement (m) and recovery (r). FIG. 3C depicts LFP power modulations for the low-frequency (left), alpha (middle), and high-beta (right) frequency bands recorded during lower limb tics from the same pair of electrodes (i.e., the first and second electrodes), averaged across all observed tics.

In TS patients, DBS is may be delivered continuously with parameter values that may be adapted or tailored for the patient, and may, for example, comprise the delivery of electrical pulse trains in the frequency range from about 100 Hz to about 130 Hz, having pulse amplitudes from about 2 V to about 5 V amplitude range, and/or having pulse widths from about 60 μs to about 120 μs.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The invention claimed is:

1. A method for treating Tourette Syndrome, the method comprising:
   acquiring an electrical neural activity signal using at least one electrode implanted in a brain of a patient and monitoring a first power of the acquired neural activity signal in a first frequency band;
   identifying an occurrence of a tic by determining whether a decrease of the first power with respect to a first baseline value for a first predetermined duration is followed by an increase in the first power with respect to the first baseline value for a second predetermined duration; and
   if the occurrence of the tic is identified, modifying a parameter of electrical stimulation to the brain according to the acquired neural activity signal.

2. The method of claim 1, further comprising:
   determining a second power of the acquired neural activity signal in a second frequency band;
   determining whether an increase of the second power for a third predetermined duration with respect to a second baseline value occurs simultaneously with the decrease of the first power; and
   if an increase of the second power with respect to the second baseline value occurs simultaneously with the decrease of the first power, modifying the electrical stimulation parameter according to acquired neural activity signal.

3. The method of claim 2, wherein the second frequency band comprises frequencies in the low-frequency band (about 2 Hz to about 7 Hz).

4. The method of claim 1, wherein the first predetermined duration is at least 250 ms, and the second predetermined duration is at least 250 ms.

5. The method of claim 1, wherein the increase in the first power is at least 2.5 times greater than the first baseline value.

6. The method of claim 1, wherein the decrease of the first power is at least 20% below the first baseline value and the following increase of the first power is at least 150% above the first baseline value.

7. The method of claim 1, wherein the first frequency band comprises frequencies in the alpha band (about 8 Hz to about 12 Hz).

8. The method of claim 1, wherein the electrical stimulation parameter is an electrical pulse frequency, and modifying the parameter value comprises assigning the electrical pulse frequency to a frequency value from about 30 Hz to about 40 Hz.

9. The method of claim 1, wherein the electrical stimulation parameter is an electrical pulse frequency, and modifying the parameter value comprises assigning the electrical pulse frequency to a frequency value that is at least 50% less than an initial electrical pulse frequency value.

10. The method of claim 1, wherein the electrical stimulation parameter is an electrical pulse width value, and modifying the parameter value comprises assigning the electrical pulse width to a width value from about 10 μs to about 30 μs.

11. The method of claim 1, wherein the electrical neural activity signal was acquired during the delivery of electrical stimulation to the brain having the electrical stimulation parameter assigned to an initial electrical stimulation parameter value, and wherein the method further comprises delivering electrical stimulation to the brain having the modified electrical stimulation parameter.

12. The method of claim 11, further comprising:
   acquiring an updated electrical neural activity signal during delivery of electrical stimulation signal having the modified electrical stimulation parameter and monitoring the first power of the updated electrical neural activity signal in the first frequency band;
   determining whether the first power has returned to approximately the first baseline value; and if the first power has returned to approximately the first baseline value, delivering electrical stimulation to the brain having the initial electrical stimulation parameter value.

13. The method of claim 12, wherein if the first power has returned to within about 50% of the first baseline value, delivering electrical stimulation to the brain having the initial electrical stimulation parameter value.

14. The method of claim 1, wherein the first power of the acquired neural activity signal in the first frequency band is determined by applying a band pass filter, followed by a rectifier, followed by applying an average filter to the acquired neural activity signal.

15. An apparatus for treating Tourette Syndrome comprising:
an implantable probe comprising an electrode; and
a stimulation device in communication with the implantable probe, wherein the stimulation device comprises:
an acquisition module in electrical communication with the implantable probe to acquire a neural activity signal from the electrode, and configured to be responsive to an acquisition processor to:
identify a tic occurrence by determining whether a decrease of a first power of the acquired neural activity signal in a first frequency band with respect to a first baseline value for a first predetermined duration is followed by an increase in the first power with respect to the first baseline value for a second predetermined duration, and
modify an electrical stimulation parameter if the tic occurrence is identified; and
a stimulation module having a voltage source or current source configured to generate and transmit to the electrode a stimulation signal in accordance with the modified electrical stimulation parameter.

16. The apparatus of claim 15, wherein identifying the occurrence of a tic further comprises determining whether a second power of the acquired neural activity signal in a second frequency band increases for a third predetermined duration with respect to a second baseline value simultaneously with the decrease of the first power.

17. The apparatus of claim 16, wherein the second frequency band comprises frequencies in the low-frequency band (about 2 Hz to about 7 Hz).

18. The apparatus of claim 15, wherein the first predetermined duration is at least 250 ms, and the second predetermined duration is at least 250 ms.

19. The apparatus of claim 15, wherein the increase in the first power is at least 2.5 times greater than the first baseline value.

20. The apparatus of claim 15, wherein the decrease of the first power is at least 20% below the first baseline value and the following increase of the first power is at least 150% above the first baseline value.

21. The apparatus of claim 15, wherein the first frequency band comprises frequencies in the alpha band (about 8 Hz to about 12 Hz).

22. The apparatus of claim 15, wherein the electrical stimulation parameter is an electrical pulse frequency, and modifying the parameter comprises assigning the electrical pulse frequency to a frequency that is from about 30 Hz to about 40 Hz.

23. The apparatus of claim 15, wherein the electrical stimulation parameter is an electrical pulse frequency and the initial electrical stimulation parameter is an initial electrical pulse frequency value, and modifying the parameter value comprises assigning the electrical pulse frequency to a frequency value that is about 50% less than the initial electrical pulse frequency value.

24. The apparatus of claim 15, wherein the electrical stimulation parameter is an electrical pulse width value, and modifying the parameter value comprises assigning the electrical pulse width to a width value from about 10 μs to about 30 μs.

25. The apparatus of claim 15, wherein the acquisition module is further configured to be responsive to the acquisition processor to:
identify a tic conclusion by determining whether the first power has returned to approximately the first baseline value, and
to revert the modified electrical stimulation parameter to an initial electrical stimulation parameter if the tic conclusion is identified.

26. The apparatus of claim 25, wherein a tic conclusion is identified if the first power has returned to within about 50% of the first baseline value.

27. The apparatus of claim 15, wherein the acquisition module circuitry comprises a band pass filter, a rectifier, and an average filter for determining the first power of the acquired neural activity signal in the first frequency band.

* * * * *